United States Patent [19]

Flom et al.

[11] 3,991,426
[45] Nov. 16, 1976

[54] POSTERIOR CHAMBER ARTIFICIAL INTRAOCULAR LENS WITH RETAINING MEANS AND INSTRUMENTS FOR USE THEREWITH

[76] Inventors: Leonard Flom, Arlen Road, Westport, Conn. 06880; Kenneth J. Rodgerson, 83 Melville Ave., Fairfield, Conn. 06430

[22] Filed: Jan. 14, 1976

[21] Appl. No.: 648,936

Related U.S. Application Data

[63] Continuation-in-part of Ser. No. 549,853, Feb. 14, 1975, abandoned.

[52] U.S. Cl. ................................ 3/13; 128/303 R
[51] Int. Cl.² .................... A61F 1/16; A61F 1/24; A61F 9/00
[58] Field of Search ............... 3/13, 1; 128/303 R; 351/160

[56] References Cited
UNITED STATES PATENTS

| | | | |
|---|---|---|---|
| 2,952,023 | 9/1960 | Rosen | 3/13 |
| 3,074,407 | 1/1963 | Moon et al. | 128/303 R |
| 3,454,966 | 7/1969 | Rosen | 3/13 |
| 3,711,870 | 1/1973 | Deitrick | 3/13 |
| 3,866,249 | 2/1975 | Flom | 3/13 |

*Primary Examiner*—Ronald L. Frinks
*Attorney, Agent, or Firm*—Wooster, Davis & Cifelli

[57] ABSTRACT

Artificial intraocular lenses comprise an optical zone portion adapted to be implanted in the posterior chamber of an eye, posts extending from said optical zone portion through the iris and into the anterior chamber thereof, and retaining means adapted to be secured to the ends of the posts, whereby said posts and retaining means hold and position the artificial intraocular lenses within the eye. In some embodiments, the posts and retaining means are configured for an interengaging press fit. In another embodiment the posts are attached to the retaining means and are adapted to be secured to the optical zone or lens portion positioned in the posterior chamber. Instruments aiding in the implanting of the artificial intraocular lenses in the eye, and in particular, in press fitting the retaining means to the posts, comprise means for supporting the retaining means on the instrument, bridle means connecting the optical zone portion of the artificial intraocular lenses with the instrument, and means for drawing the posts of the optical zone portion toward the retaining means until the desired interengaging press fit therebetween is achieved. The instruments are also adapted to attach the posts of the retaining means to the lens portion in the other embodiment referred to above, in a similar manner. The instruments are also modified to remove the retaining ring from the posts.

61 Claims, 32 Drawing Figures

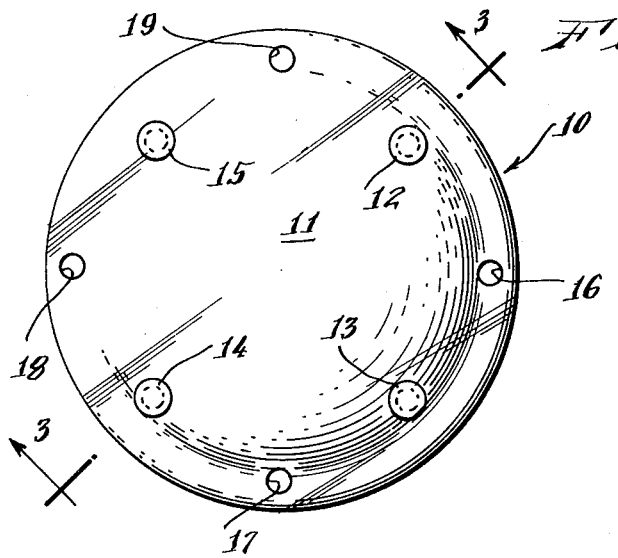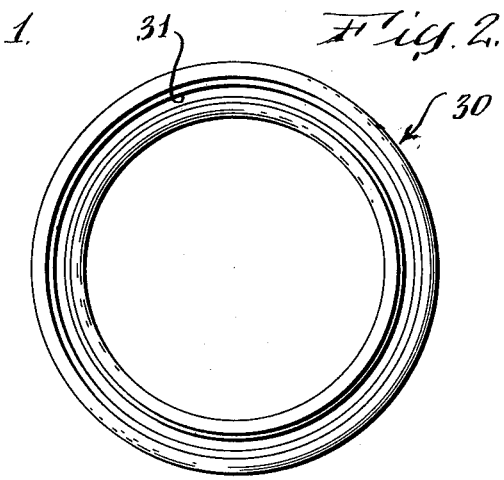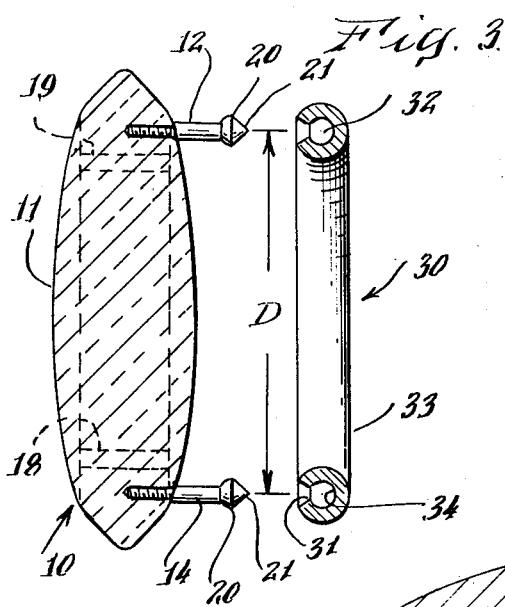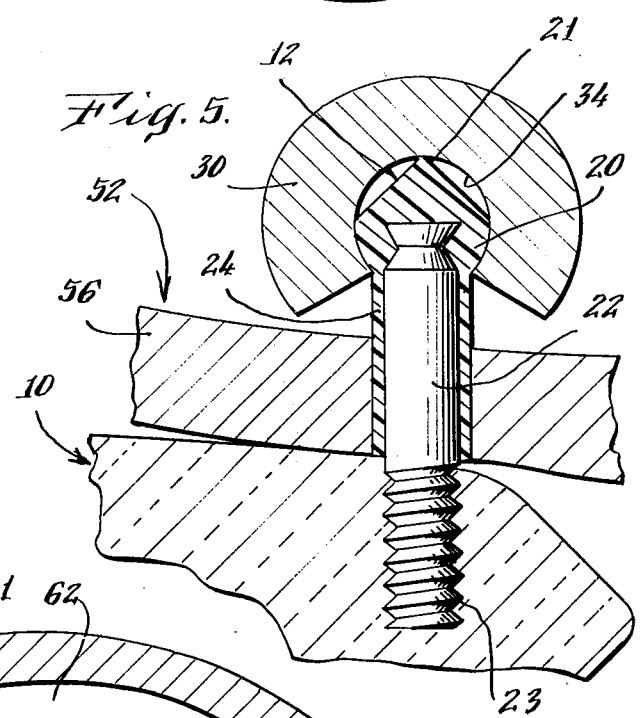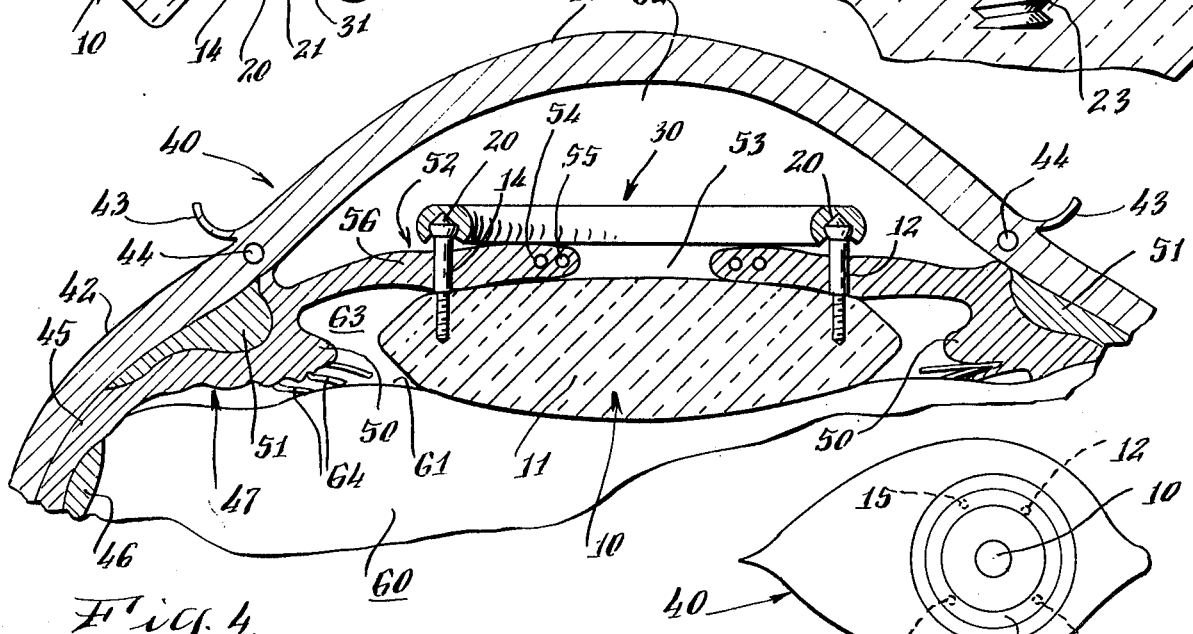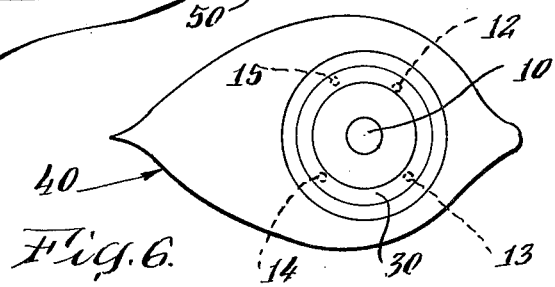

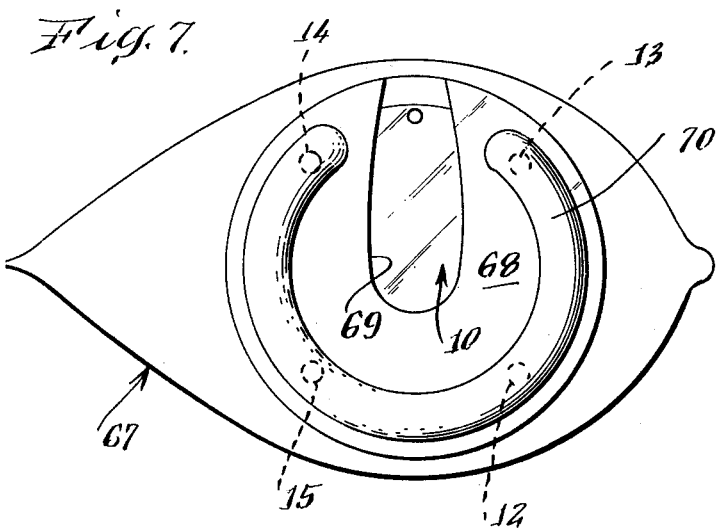
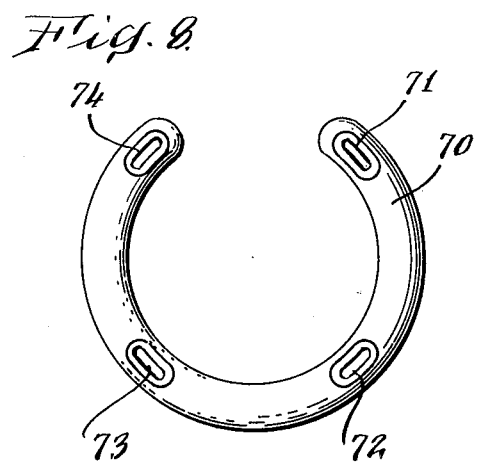
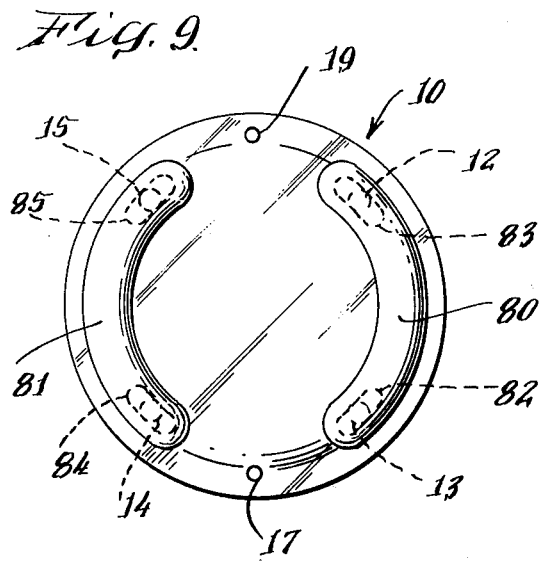
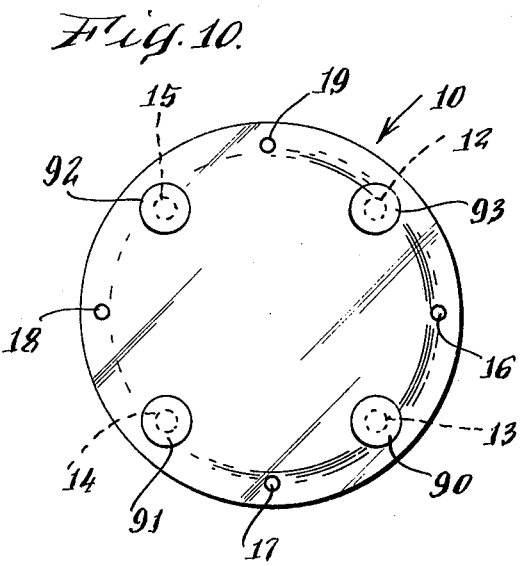
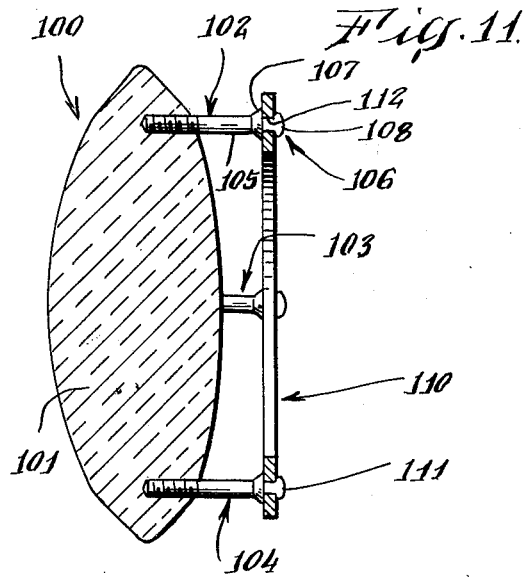
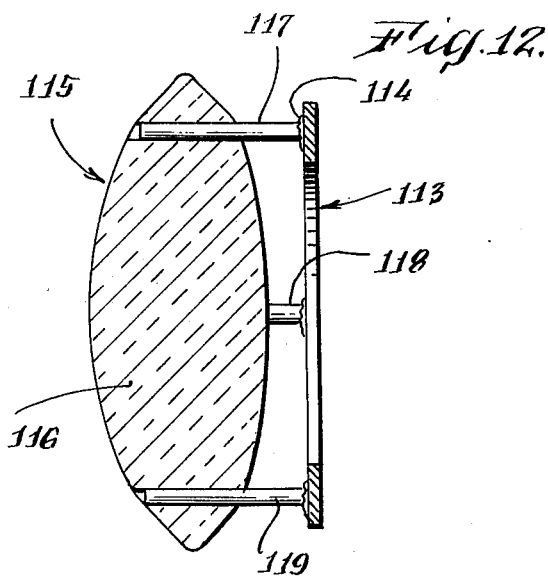

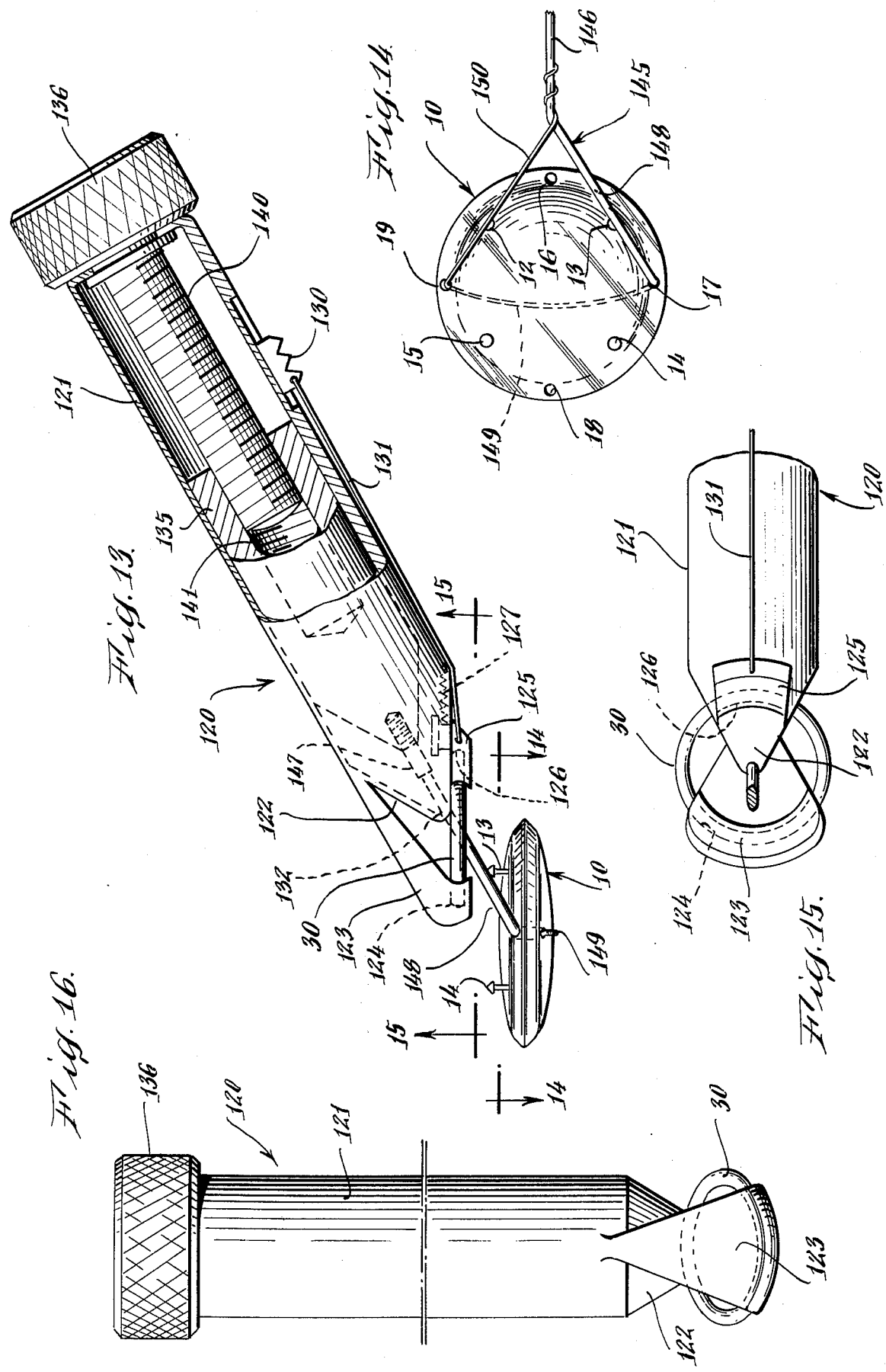

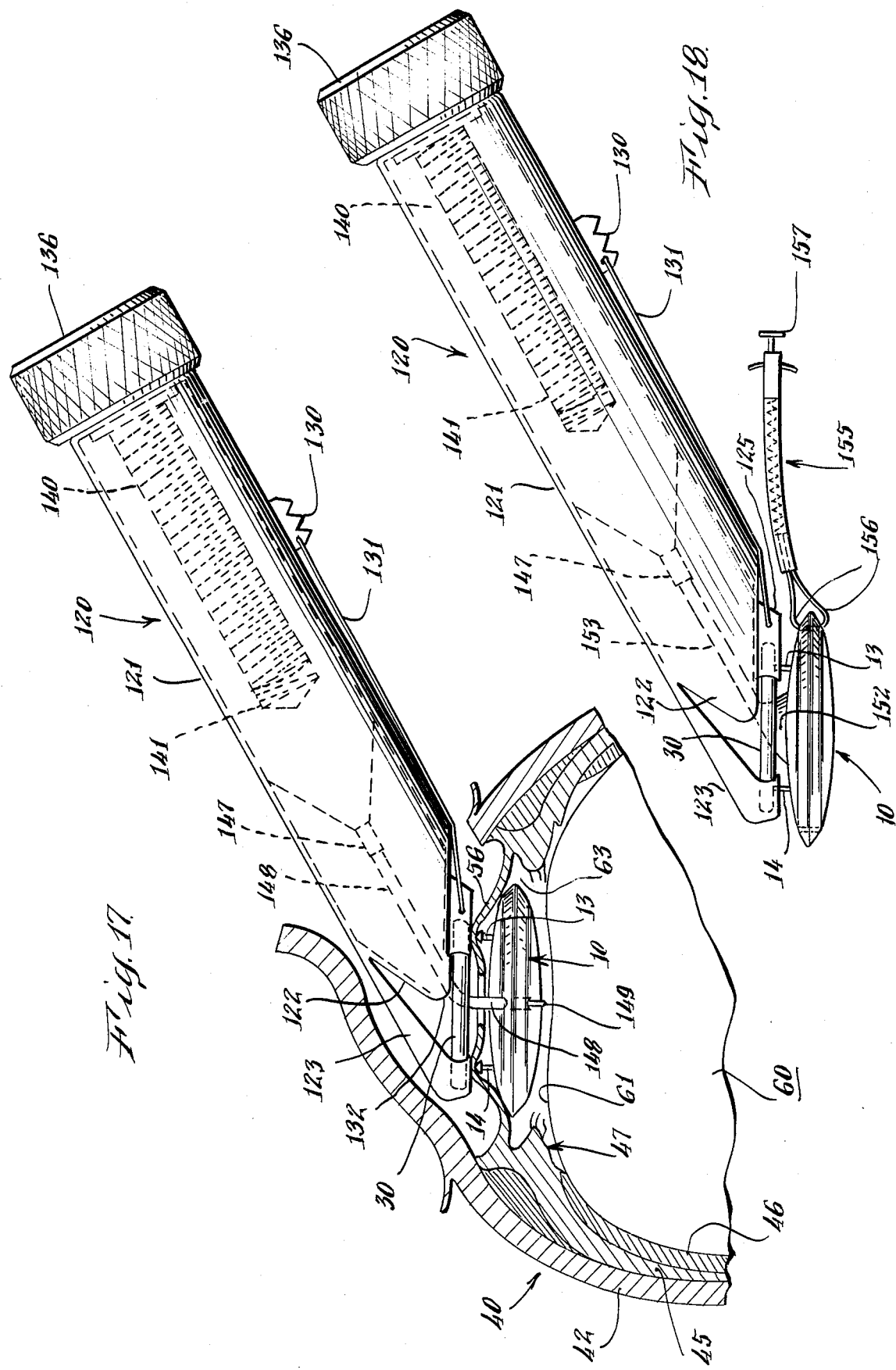

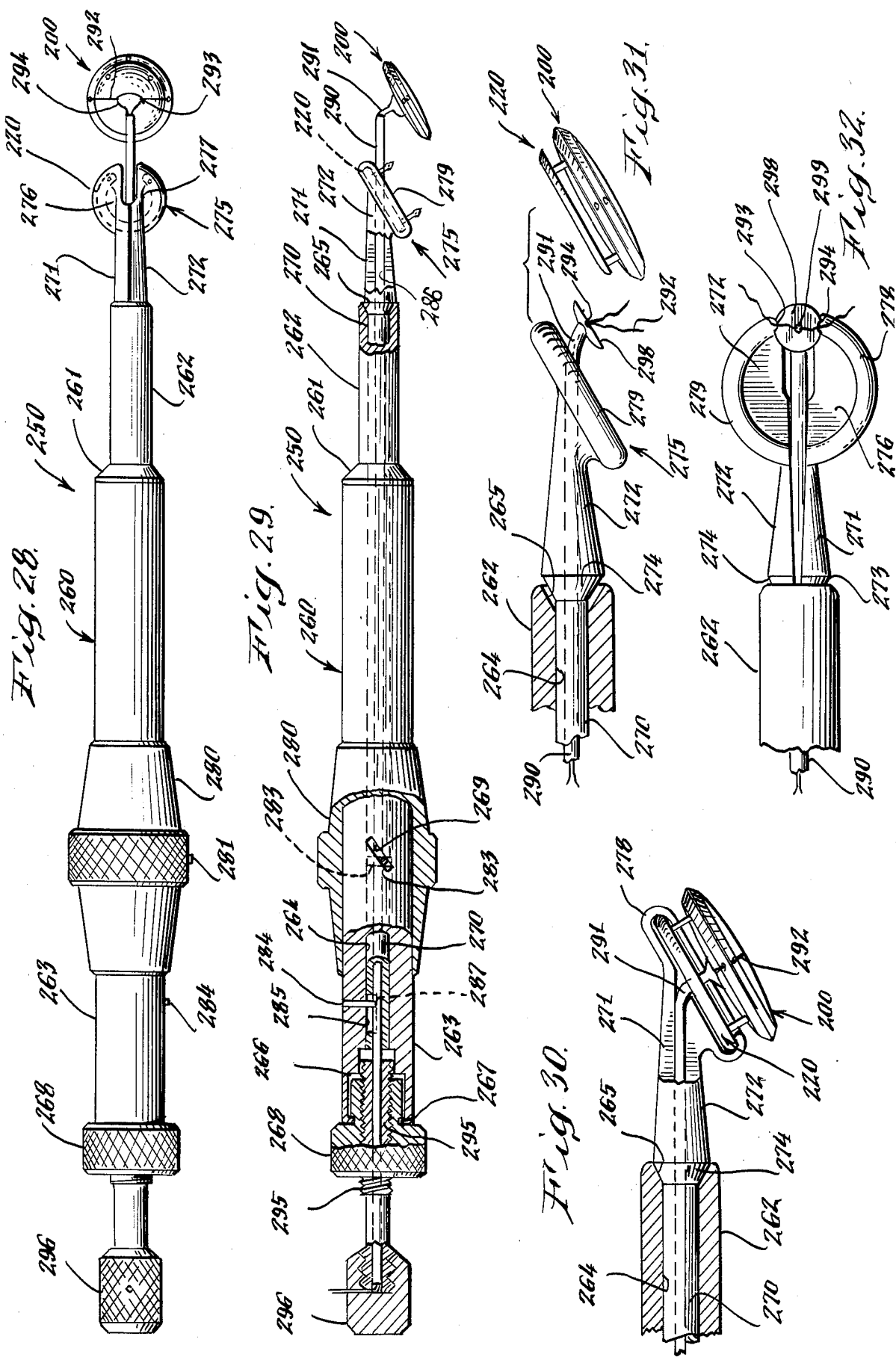

POSTERIOR CHAMBER ARTIFICIAL INTRAOCULAR LENS WITH RETAINING MEANS AND INSTRUMENTS FOR USE THEREWITH

This application is a continuation-in-part of our application, Ser. No. 549,853, filed Feb. 14, 1975 and now abandoned.

BACKGROUND

1. Field of the Invention

This invention relates to an artificial intraocular lens for implantation in the posterior chamber of the eye to obviate aphakia, the lens including retaining means, and further relates to instruments for implanting and removing the artificial intraocular lens, including respectively attaching and detaching the retaining means.

2. Prior Art

When no lens is present in the eye, which is known as the aphakic condition or aphakia and is usually the result of intracapsular or extracapsular lens extraction, the eye does not have the ability to focus rays of light. Therefore, the eye receives a blurred image and vision is impaired.

The most common solution for providing a focusing mechanism to obviate the aphakic condition is to interpose contact lenses or spectacles or a combination thereof between the eye and the light entering therein. However, both contact lenses and spectacles have drawbacks when used in the treatment of aphakia. Neither spectacles nor contact lenses can duplicate the natural optical system because they are positioned outside of the eye, which results in a shift of the optical center from the in vivo state. Because the optical center has been shifted, the image received by the eye is either distorted and/or changed in size. In particular, spectacles and/or contact lenses usually cannot be used to restore exactly binocular vision after removal or loss of the lens from one eye when the other eye continues to function normally.

Further, the most common reason for removal of a lens is the condition of lenticular opacity known as a cataract, which occurs primarily in aged persons who have difficulty in adjusting to contact lenses and in manipulating the contact lenses for insertion and removal. Cataracts are also common in animals, such as dogs and horses, and contact lenses and/or spectacles are not suitable devices for their treatment.

The desirability of implanting an artificial lens within the eye to obviate the condition of aphakia is well-known and accepted in countries such as England, Holland and Italy. However, practical devices for carrying out this desirable objective have not been perfected, although several devices have been used with a modicum of success.

In approximately 1950 Harold Ridley developed an artificial intraocular lens which comprised an optical lens portion having three foot-like projections or "feet" extending radially outward therefrom. Ridley originally placed this lens in the posterior chamber of the eye, behind the iris, with the feet resting against the ciliary body between the ciliary process and the base of the iris. However, positioning of this lens in the posterior chamber was abandoned because of instances of dislocation after implantation and failures from glaucoma and the like, probably caused by irritation of the ciliary body by the feet.

Ridley's failure with posterior chamber artificial lenses led him and others, such as D. P. Choyce, to turn their attention to intraocular artificial lenses implanted in the anterior chamber of the eye between the iris and the cornea. The particular lens used was similar to Ridley's original lens, and had radially protruding feet which accomplished positioning of the lens in front of the pupil. These efforts also met with limited success, primarily because of the problems of irritation of the eye by the supporting feet and dislocation of the lens from its desired position in front of the pupil.

It should be noted that placement of the lens in the anterior chamber is an unnatural position, with the attendant problems of restoring accurate binocular vision. Also, an anterior chamber lens is not positioned adjacent to the hyaloid membrane for supporting the vitreous humor, and instances of forward displacement of the vitreous humor and retinal detachment are more likely to occur when anterior chamber lenses are used.

E. Epstein and C. D. Binkhorst developed artificial intraocular lenses which rely on the constrictor muscle of the iris as the positioning mechanism. Eppstein first designed a "collar-stud" implant, with the pupil constricted in its waist for positioning thereof. Copeland's "Maltese Cross" pupil-supported implant has two leaves anterior to the iris and two leaves at right angles to the others and behind the iris. Binkhorst developed an iridocapsular (two-loop) lens and an iris-clip (four-loop) lens. The former comprises a lens of larger diameter than the pupil and placed thereover so that the periphery engages the front of the iris, and further comprises two metal loops which protrude from the back of the lens and extend generally parallel with the back surface of the lens and behind the iris for clipping the lens to the iris. Binkhorst's iris-clip lens is similar except that the iris is held by two pairs of loops which flank the iris and support the lens in front of the pupil. In some instances, the iris is sutured to the clips to secure the positioning of the lens. This type of lens is also unsatisfactory in several respects. It, by necessity, interferes with constriction of the pupil, and in fact fixes the size of the pupil. It is also an anterior chamber lens, wherein correct positioning of the optical center cannot be achieved.

J. G. F. Worst considered posterior placement of an artificial lens to be desirable, but developed a lens having a pair of closely spaced openings for positioning in front of the iris. A suture was placed through the two openings and attached the lens to the iris. Although it is not believed that Worst's suture would cause irritation of the ciliary body, as did the earlier posterior lens of Ridley, the difficulty of the technique necessary to suture the lens in position without damaging the iris as well as the possibility that the suture would not hold or would tear out from the iris has limited the acceptance of Worst's lens.

Additional artificial lenses designed for positioning in the posterior chamber are described in U.S. Pat. No. 3,711,870 to Deitrick and in U.S. Pat. No. 3,673,616 to Fedorov et al. Deitrick's lens comprises a central optical portion surrounded by a resilient silicone flange shaped to receive and nest against the ciliary body. The lens is to be held in place by suturing the resilient flange to the ciliary body. Although the medical worth of the Deitrick lens is not yet known, it is known that it would be difficult to place sutures where Deitrick directs and it is also known the there may be reluctance on the part of ophthalmologists or ophthalmologic surgeons to do so because of the many risks attendant with the irritation of the ciliary body. Fedorov et al's lens is supported in the eye by radially protruding prongs flanking the iris and gripped by the constrictor muscles of the iris adjacent to the pupil, in somewhat the same manner as the Binkhorst lens.

Several of the prior art lenses are discussed in an article by D. P. Choyce entitled "History of Intraocular Implants" which is printed in Annals of Ophthalmology, October, 1973. The article also includes a list of references from which further information concerning prior art intraocular lenses can be obtained.

Several of the above lenses rely on sutures placed in the iris for holding the lenses in position. It should be noted that the iris consists of spongy, flexible tissue which may be pulled and stretched to a limited degree without damaging it. However, the iris has the unique property of never healing together after being cut or damaged. Thus, if a suture pulls through the iris, the damage to the iris is permanent. Because sutures are generally of a small diameter, if a lens positioned and held by sutures is subjected to a dislocating force, the sutures may cut the iris, resulting in permanent damage.

SUMMARY OF THE INVENTION

The artificial intraocular lens according to the invention herein is adapted for implantation in the posterior chamber, wherein all the advantages of natural positioning of the lens are achieved. The artificial intraocular lens is held in place by a plurality of posts extending forwardly from the lens and protruding through the iris into the anterior chamber. Retaining means are secured to the posts in the anterior chamber of the eye adjacent to the iris. In a first embodiment, the retaining means preferably comprises a retaining ring which is press fit onto the ends of the posts in the anterior chamber, although the retaining means may comprise a partial ring or even individual retaining members for each post. In another embodiment, the posts are integral with the retaining means, which may be a whole or partial ring, and the posts are inserted through the iris and press-snap fit into openings in the lens.

In both embodiments, the iris is held loosely constrained between the artificial intracular lens and the retaining means with the posts extending through the iris, whereby the artificial intraocular lens is held in the desired position. The retaining means are arrayed about and separated from the pupil and do not interfere with vision. Openings through the artificial intraocular lens are provided near the periphery to permit the free flow of aqueous, which is produced by the ciliary body, and to aid in the manipulation and implantation of the artificial intraocular lens.

Thus, the artificial intraocular lens according to the invention herein is firmly held in a natural position, which is the posterior chamber of the eye. The artificial intraocular lens according to the invention herein avoids any contact with the ciliary body, presents a smooth surface to the endothelium of the cornea as well as to the hyloid muscles of the iris adjacent to the pupil, and does not contact the area of Schlemm's canal. Thus, these and any other sensitive anatomical areas of the eye are not irritated by the artificial intraocular lens according to the invention herein. True binocular vision may be achieved with the posterior chamber artificial intraocular lens according to the invention herein, and forward displacement of the vitreous humor and consequent cystoid macular endema and/or retinal detachment are avoided.

Instruments are also provided for implanting the artificial intraocular lenses. These instruments make the techniques for implantation within the range of capability of the average ophthalmological surgeon.

A first embodiment of an instrument according to the invention herein and well adapted for use with the first embodiment of the artificial intraocular lenses generally comprises a handle configured to hold the retaining ring, or other retaining means adapted to press fit onto the posts of the artificial intraocular lens. A bridle attaches the artificial intraocular lens to a member slidably mounted in the instrument with respect to the retaining ring. The bridle is sufficiently rigid to aid in inserting the artificial intraocular lens through the dilated pupil and into the posterior chamber. A thumbwheel or other controlled adjusting mechanism is provided to drive the slidably mounted member and to thereby cause relative movement of the retaining ring into position over the posts of the artificial intraocular lens, and finally to press fit the retaining ring onto the posts. Means are provided to release the retaining ring from the instrument and the bridle can be easily severed, whereafter the instrument can be removed, leaving the artificial intraocular lens and attached retaining means implanted within the eye.

The instrument may also be provided with a rigid forwardly protruding foot attached to the slidably mounted member, wherein by reversing the rotation of the thumbwheel or other drive means, the retaining ring can be lifted from the posts to release the artificial intraocular lens for removal. A lens snare may also be provided to aid in extracting the lens.

A second embodiment of an instrument according to the invention herein is particularly well adapted for implanting the artificial intraocular lens in which the posts are integral with the retaining ring and press-snap fit into the lens. The second embodiment instrument also comprises a handle configured to releasably hold the retaining ring. A thin member is slidably mounted in the handle, extends therefrom through the held ring, and terminates in a foot against which the lens is tightly secured by a thin bridle. Thumbwheel or other adjusting means are provided to drive the slidably mounted rod, causing relative movement of the retaining ring toward the lens until the posts engage the openings in the lens which receive them, and thereafter press-snap joining the retaining ring and the lens. The foot of the thin member, against which the lens is tightly held, accurately positions the lens with respect to the posts of the retaining ring, which is an important feature inasmuch as the lens is blocked from view behind the iris when the lens and ring are joined. The foot also serves to separate the retaining ring from the lens, should removal be necessitated.

OBJECTS OF THE INVENTION

It is a principal object of the invention to provide an artificial intraocular lens for obviating aphakia.

It is another object of the invention to provide an artificial intraocular lens for implantation into the posterior chamber of the eye.

It is a further object of the invention to provide an artificial intraocular lens which includes means for positioning and holding it within the eye without irritating sensitive portions of the eye.

It is a further object of the invention to provide an artificial intraocular lens and instruments for implanting the same which permit an implantation technique within the range of skills of the average ophthalmological surgeon.

Other and more particular objects of the invention will be in part obvious and will in part appear from a perusal of the following description of the preferred embodiment and the claims, taken together with the drawings.

DRAWINGS

FIG. 1 is a front elevation view of an artificial intraocular lens according to the invention herein;

FIG. 2 is a rear elevation view of a retaining ring according to the invention herein for the artificial intraocular lens of FIG. 1;

FIG. 3 is a sectional view of the artificial intraocular lens of FIG. 1 and the retaining ring of FIG. 2;

FIG. 4 is a sectional view of an eye showing the artificial intraocular lens and retaining ring of FIG. 3 implanted therein;

FIG. 5 is a fragmentary enlarged sectional view of a portion of the eye of FIG. 4 having the artificial intraocular lens and retaining ring implanted therein;

FIG. 6 is a front elevation view of the eye of FIG. 4 having the artificial intraocular lens and retaining ring implanted therein;

FIG. 7 is a front elevation view of another eye having the artificial intraocular lens and a partial retaining ring according to the invention herein implanted therein;

FIG. 8 is a rear elevation view of the partial retaining ring of FIG. 7;

FIG. 9 is a front elevation view of the artificial intraocular lens and dual retaining members according to the invention herein;

FIG. 10 is a front elevation view of the artificial intraocular lens and plural retaining buttons according to the invention herein;

FIG. 11 is a sectional view of another embodiment of an artificial intraocular lens and a retaining ring therefor according to the invention herein;

FIG. 12 is a sectional view of another embodiment of an artificial intraocular lens and a retaining ring therefore according to the invention herein;

FIG. 13 is a side elevation view, partially in section, of an artificial intraocular lens, a retaining ring therefor, and an instrument for implanting the same within an eye, all according to the invention herein;

FIG. 14 is a sectional view taken along the lines 14—14 of FIG. 13 showing a top plan view of the artificial intraocular lens held by a bridle;

FIG. 15 is a sectional view taken along the lines 15—15 of FIG. 13 showing a bottom plan view of the instrument and the retaining ring held thereby;

FIG. 16 is a front elevation view of the instrument of FIG. 13 and the retaining ring held thereby;

FIG. 17 is a side elevation view, partially in section, of the artificial intraocular lens and the retaining ring being implanted into an eye with the instrument of FIG. 13;

FIG. 18 is a side elevation view of an artificial intraocular lens having a retaining ring attached thereto, and the instrument of FIG. 13, said instrument modified for removing the retaining ring from the artificial intraocular lens, all according to the invention herein;

FIG. 28 is a top plan view of an artificial intraocular lens, a retaining ring therefor, and an instrument for implanting the same within an eye, all according to the invention herein;

FIG. 29 is a side elevation view, partially in section, of the artificial intraocular lens, retaining ring and instrument of FIG. 28;

FIG. 30 is a fragmentary view, partially in section, of the artificial intraocular lens, retaining ring and instrument of FIG. 28 showing the lens and retaining ring joined;

Figure 19:
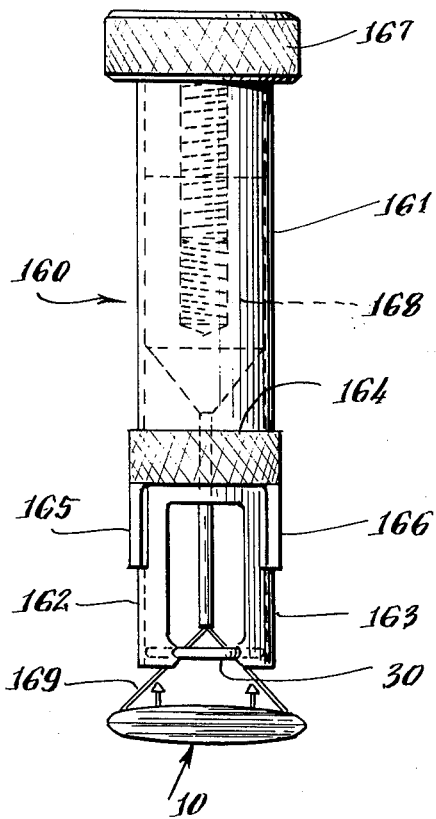
FIG. 19 is a side elevation view of an artificial intraocular lens, a retaining ring therfore, and another instrument for implanting the same within an eye, all according to the invention herein.

FIG. 31. is a fragmentary view, partially in section, of the artificial intraocular lens, retaining ring and instrument of FIG. 28 showning the lens and retaining ring release from the instrument; and FIG. 32 is a bottom view of the instrument of FIG. 28 corresponding to FIG. 31.

The same reference numbers refer to the same elements throughout the various Figures.

PREFERRED EMBODIMENTS

The invention herein relates to an artificial intraocular lens including retaining means for securing the artificial intraocular lens in an eye, several embodiments of which will be described, and to instruments aiding in implanting the artificial intraocular lenses in eyes, and in particular in attaching the retaining means to the implanted artificial intraocular lens, several embodiments of which also will be described.

Referring now to FIGS. 1 – 3, there is shown an artificial intraocular lens 10 and a retaining ring 30 for use with the artificial intraocular lens 10, according to the invention herein.

The artificial intraocular lens 10 (hereinafter often referred to as the "lens") generally comprises an optical zone portion 11 and a plurality of posts 12 – 15 which, in cooperation with retaining means, anchor the lens 10 in an eye. A plurality of openings 16 – 19 may be provided through the optical zone portion of the lens near the periphery thereof.

The optical zone portion 11 can be either a biconvex or planoconvex lens, as required. It is preferable that the optical zone portion be shaped similar to the natural intraocular lens insofar as is possible. The optical zone portion is preferably round in plan view and may have a diameter of 8 to 10 millimeters, which is also the overall diameter of the lens 10; however, the diameter is merely suggested and is approximately the same diameter as a human natural ocular lens, and it should be rocognized that the artificial intraocular lens can and should be sized according to the eye into which it is to be implanted. The optical power of the optical zone portion 11 of the lens 10 generally is in the range of 13 to 17 diopters, with the final decision as to the exact optical power resting with the ophthalmologic surgeon who has examined the patient and is prescribing the lens. The optical zone portion 11 is preferably fabricated of a medical grade of either polymethyl methacrylate or silicone, or of another material suitable for implantation in the eye and having the requisite clarity and index of refraction for use as a lens material.

With reference to FIG. 1, the posts 12 – 15 are positioned at 90° intervals on a circle concentric with and near the periphery of the lens 10, the circle having a diameter D. Referring now to FIG. 3, the posts 12 – 15 protrude forwardly from the optical zone portion 11, and the tip of each post, for instance, post 12, is provided with an enlarged head 20 including a substantially hemispherical inner portion and a conical outer portion converging to a slightly rounded tip 21. As best seen in FIG. 5, in which the post 12 is shown in an enlarged sectional view, the post 12 comprises an inner stud 22 which is threaded at its lower end 23 into the optical zone portion 11 of the lens 10. A jacket 24 surrounds the protruding portion of stud 22 and comprises the enlarged head 20. The stud 22 is preferably fabricated of gold and the jacket 24 is preferably fabricated of either a medical grade of polymethyl methacrylate or silicone, or of another plastic material suitable for implantation in the eye. The remaining posts 13 – 15 are similar to post 12.

The openings 16 – 19 are also located at 90° intervals on a circle concentric with and near the periphery of the lens 10, and each opening is further located 45° from each of the adjacent posts. The openings 16 – 19 are utilized in connection with means for holding and manipulating the lens 10 during implantation and/or removal thereof, and provide drain holes for aqueous produce by the ciliary body when the lens 10 is implanted in an eye.

Referring now to FIGS. 2 – 6, the retaining ring 30 is round in plan view and has an outer surface 33 which is circular in cross section. The circular outer surface is interrupted by a V-shaped slot 31 which extends around the entire retaining ring on one side thereof. The V-shaped slot 31 connects the outer surface of retaining ring 30 with an annular inner space 32 define by the inner surface 34 of the retaining ring 30. The inner surface 34 is also circular when viewed in cross section and is concentric with the outer surface 33 of retaining ring 30. The annular space 32 and the V-shaped slot together form a slot extending entirely about the retaining ring on one side thereof, and this slot has a key hole configuration in section, being constricted at the intersection of the inner end of the V-shaped slot 31 and the annular inner space 32, as best seen in FIG. 3.

The retaining ring 30 is slightly resilient, so that the V-shaped slot 31 can be expanded to admit the heads of the posts 12 – 15. The retaining ring 30 is preferably fabricated of a medical grade of polymethyl methacrylate, silicone, or other slightly resilient material suitable for implantation in the eye. It may be either clear or tinted, as desired for cosmetic purposes.

The retaining ring 30 is adapted to be press fit onto the posts 12 – 15 and to be retained thereon by the interengaging structure of the posts and retaining ring. In particular, the means diameter D of the V-shaped slot 31 corresponds to the diameter between opposite posts, such as posts 12 and 14, so that the points of the heads of the posts may be centrally received in the V-shaped slot 31. As the retaining ring 30 is pressed on to the posts 12 – 15, the conical outer portions of the heads of the posts enter the V-shaped slot and expand it until the retaining ring snaps over the heads of the posts. As best seen in FIGS. 4 and 5, the inner surface 34 of the retaining ring adjacent to the V-shaped slot 31 engages the hemispherical inner portions of the heads of the posts, whereby the retaining ring is secured to the posts by an interengaging fit therebetween.

Referring now to FIG. 4, there is shown an eye 40 having the artificial intraocular lens 10 and retaining ring 30 described above implanted therein. The eye 40 comprises a transparent cornea 41 which connects with the sclera 42, better known as the white of the eye. The sclera extends substantially around the entire eye except for the region of the cornea. A thin membrane 43, which is known as the conjunctiva, extends from the cornea to the underside of the eye lid, not shown. Schlemm's canal, indicated at 44, is located near the intersection of the cornea, sclera and conjunctiva. In the rear portions of the eye, not fully shown, the choroid 45 overlays the interiro surface of the sclera and the retina 46 overlays the inner surface of the choroid. Near the front of the eye the choroid joins with the ciliary body, generally indicated at 47, which includes the ciliary process 50 and the ciliary muscle 51. Extending from the ciliary body is the iris 52 which defines the pupil 53. The choroid, ciliary body and iris are together known as the uveal tract, which is a vascular tract surrounding most of the eye.

The interior of the eye is substantially filled with vitreous humor 60, and the hyloid membrane 61 covers the surface of the vitreous humor. The anterior chamber of the eye is indicated at 62 and is located between the front of the iris and the cornea 41. The posterior chamber of the eye, indicated at 63, is located between the iris and the vitreous humor. The natural lens, not shown in the drawings herein, occupies the posterior chamber 63 and is held in place by zonules 64, which are shown cut as they would be during removal of the natural lens.

Referring now particularly to the iris 52, it defines the pupil 53 by virtue of a central opening therein. Sphincter and dilator muscles 54 and 55 are located in the iris adjacent to the inner periphery thereof, and control the size of the pupil. The primary expansion and constraction of the tissue of the iris takes place in the vicinity near the sphincter and dilator muscles. The stroma 56 of the iris extends between the ciliary body and the inner portion of the iris including the sphincter and dilator muscles. The stroma tissue passively folds in an accordian-like manner during dilation and contraction of the pupil. The iris tissue, including the stroma, is quite flexible and can be pulled and stretched. However, the iris has the unique property of not healing if torn or damaged. Accordingly, care should be taken in manipulating the iris.

In order to implant the artificial intraocular lens 10 and retaining ring 30 therefor, an incision is made in the cornea near Schlemm's canal, and the cornea is folded back. If implantation of the artificial intraocular lens is being undertaken because of a cataract condition, it is preferable to perform the natural lens removal and the implantation of the artificial intraocular lens in the same operation. Accordingly, the first step after opening an incision and laying back the cornea may be to perform an intracapsular or extracapsular extraction, as the condition of the patient dictates. It is anticipated that better results can be achieved in restoring vision with an artificial intraocular lens according to the invention herein if the entire natural lens is removed.

The pupil can be dilated sufficiently through the use of drugs to permit passage of the artificial intraocular lens 10 through the pupil into the posterior chamber 63 of the eye. After the lens 10 has been inserted into the posterior chamber of the eye, the posts 12 – 15 of the lens 10 may be pushed through the iris, taking care to position the iris so that the head of each post is inserted through the stroma tissue at approximately the point where it would natually fall with the pupil in a normal condition, i.e. not dilated by drugs. The retaining ring 30 is then press fit onto the posts 12 – 15 as described above, so that the retaining ring is firmly secured upon the posts, as illustrated in FIGS. 4 – 5. The ophthalmologic surgeon may then close the eye in accordance with ordinary ophthalmologic surgical techniques.

It should be noted that the posts have a length of approximately 1 ½ to 2 millimeters, whereby the retaining ring 30 is sufficiently spaced from the lens 10 so that the iris is not pinched orr constricted, which would disrupt circulation to the inner portions of the iris near the pupil and the constrictor and dilator muscles. The structure of the artificial intraocular lens 10 and the retaining ring 30 holds the lens firmly in the eye. In particular, the posts which extend through the iris hold the lens against lateral displacement toward the edges of the eye, and an entire ring of the stroma tissue is loosely embraced between the lens and the retaining ring to prevent the posts from pulling back through the iris. The lens is nestled against the hyloid membrane, retaining the vitreous humor from forward displacement and thereby minimizing the danger of cystoid macula endema or retinal detachment.

It should be note that the artificial intraocular lens and retaining ring therefor, when implanted in an eye as illustrated in FIG. 4, do not comprise five key ocular anatomical areas, to wit: the endothelium or backside of the cornea; Schlemm's canal; the dilator and constrictor musclles of the pupil; the ciliary body; and the vitreous humor and hyloid membrane. By avoiding there key areas of sensitivity, complications after the implantation of the artificial intraocular lens and retaining ring are greatly reduced. The artificial intraocular lens is positioned in the posterior chamber of the eye, thereby closely duplicating the natural state and providing for restoration of good binocular vision.

Referring now to FIG. 6, the eye 40 is shown with the artificial intraocular lens 10 and retaining ring 30 implanted therein. From FIG. 6 it is apparent that the anchoring means for the lens 10 comprising the posts 12 – 15 and retaining ring 30 do not interfere with normal vision through the pupil 53.

Referring now to FIG. 7, there is shown an eye 67 wherein a sector iridectomy has been performed on the iris 68 thereof to enlarge the pupil 69 so that it extends to the periphery of the iris. The artificial intraocular lens 10 has been implanted in the eye 67 with the posts 12 – 15 arranged so that posts 13 and 14 flank the enlarged portion of pupil 69 created by the sector iridectomy. A retaining member 70 is provided for the lens 10, and the retaining member 70 comprises slightly more than three-fourth of an entire ring. The retaining member 70 is secured to the posts of lens 10 so that the enlarged pupil 69 is not blocked by the retaining member. Referring now to FIG. 8, which is a rear plan view of the retaining member 70, it can be seen that four openings 71 – 74 are provided to receive the posts 12 – 15 of the lens 10. The openings 71 – 74 are preferably slightly enlongated, permitting some latitude in positioning the retaining member 70 on the posts of the lens 10. The openings 71 – 74 have a cross-sectional shape which may be similar to that shown in FIGS. 3 – 5, wherein the heads of the posts 12 – 15 may be accommodated and secured by an interengaging fit between the posts and the retaining member 70. The lens 10 is adequately held in the eye by the posts 12 – 15 and the retaining member 70, and the five key anatomical areas of the eye are protected.

Referring now to FIG. 9, the artificial intraocular lens 10 is shown with another retaining means, which comprises two retaining members 80 and 81. The retaining member 80 is curved and comprises somewhat more than one-fourth of a complete ring. It is provided with elongated openings 82 and 83 positioned, respectively, near its ends for receiving and holding the posts 12 and 13 of the artificial intraocular lens 10 through an interengaging fit. The retaining member 81 is similarly provided with openings 84 and 85, which receive, respectively, posts 14 and 15. The retaining members 80 and 81 may be used with the artificial intraocular lens in implantation situations involving sector and peripheral iridectomies as well as in implantation situations in which no iridectomy is involved. A substantial portion of the stroma tissue of the iris is lossely constrained between the retaining members 80 and 81 and the lens 10, wherein the lens is adequately held in position with the eye by the posts 12 – 15 and the retaining members 80 and 81, and the posts 12 – 15 are prevented from pulling back through the iris. The five key anatomical areas of the eye are fully protected when retaining members 80 and 81 are used with the lens 10.

Referring now to FIG. 10, the artifical intraocular lens 10 is shown together with a further embodiment of retaining means, which comprise four individual retaining buttons 90 – 93. Each of the retaining buttons 90 – 93 is substantially hemispherical and has an opening in its underside for receiving one of the heads of one of the posts 12 – 15 of the lens 10 in an interengaging fit whereby the retaining buttons 90 – 93 may be press fit on to the posts 12 – 15 and remain secured thereon. The retaining buttons 90 – 94 do not embrace as much of the stroma tissue between them and the lens 10 as do the previously described retaining members, but nevertheless the posts 12 – 15 and retaining buttons 90 – 93 do provide for sufficient anchoring of the artificial intraocular lens within the eye and effectively prevent the posts from pulling back through the iris.

Referring now to FIG. 11, there is shown an artificial intraocular lens 100 according to the invention herein. The lens 100 comprises an optical zone portion 101 having interiorly threaded openings for receiving posts 102 – 104, which protrude forwardly from the optical zone portion 101. A fourth post is not shown in FIG. 11 because the lens is shown in section, and the four posts are deployed at 90° intervals on a cycle concentric with the periphery of lens 100 when viewed in plan. The post 102 comprises a stud portion 105 which is treaded along its lower end whereby the post is turned into one of the openings in the optical zone portion 101. The stud portion 105 extends forwardly from the optical zone portion 101 to a head portion 101 to a head portion of the post 102, generally indicated at 106. The head portion comprises a flange 107 which protrudes radially outwardly from the post and provides a shoulder surrounding the post. Separated from the shoulder is a rounded tip 108. The other posts 103 and 104 are similar to post 102.

A retaining disc 110 for use with the artificial intraocular lens 100 comprises a flat annular disc having four openings formed therethrough. Openings 111 and 112 can be seen in FIG. 11, and the openings are positioned about the retaining disc 110 for receiving the heads of the posts of the artificial intraocular lens 100. The retaining disc 110 is preferably fabricated of a slightly resilient material, and the round tips of the posts may be popped through the openings formed in the retaining disc wherein the retaining disc is seated against the flanges of the posts and held in that position by the round tips of the posts, as shown in FIG. 11. The posts themselves may be fabricated entirely of plastic, or may comprise an inner metal stud.

The artificial intraocular lens 100 and the retaining disc 110 may be implanted in an eye in a manner similar to that described above with respect to lens 10. The posts protruding through the iris and the retaining disc serve to anchor and position the lens 100 in the eye, while protecting the five key sensitive anatomical areas of the eye.

Referring now to FIG. 12, there is illustrated another artifical intraocular lens 115 according to the invention herein. It comprises an optical zone portion 116 having a plurality of posts, including post 117 – 119, extending forwardly therefrom. The posts may be fabricated entirely of plastic, such as polymethyl methacrylate, as may the lens itself. The posts snugly seat in openings in the optical zone portion 116 of the lens 115 and are secured therein by sonic welding.

A retaining disc 113 is provided for use with the artificial intraocular lens 115. The retaining disc 113 comprises a flat annular disc which may be secured to the posts, after the lens has been implanted in an eye and the posts have been pushed through the iris, by positioning the retaining disc on the ends of the posts and either sonic welding the retaining disc to the posts, or by melting the retaining disc 113 and the post together through the use of a laser, as is indicated at 114. This technique is believed to be viable inasmuch as lasers are commonly used in surgery of a delicate nature, and particular in eye surgery.

The artificial intraocular lens 115 and the retaining disc 113, being secured together by either laser or sonic welding, do not require any press fit operations to be accomplished within the eye, as do the other embodiments of artificial intraocular lenses and retaining members therefor described above. The lens 115 and retaining disc 113 have all the advantages of the previous embodiments. In particular, a substantial annular portion of the stroma is loosely embraced between the lens and the retaining disc, and the posts and the retaining disc together anchor and position the lens within the eye to prevent the posts from pulling through the iris. The sensitive areas of the eye are not disturbed by the artificial intraocular lens 115 and retaining disc 113.

This invention also relates to instruments for inserting artificial intraocular lenses as described above into the eye, and in particular, for press fitting the retaining members on the posts of the artificial intraocular lens. The invention further relates to instruments which may be used for removing the retaining members from the posts, if necessary.

Referring now to FIG. 13, there is shown an instrument 120 according to the invention herein. The artificial intraocular lens 10 and the retaining ring 30 therefor are shown attached to the instrument 120, as will be more fully discussed below.

The instrument 120 comprises a tubular handle 121 whih terminates at its lower end in a conical tip 122. As best seen in FIGS. 13, 15 and 16, a finger-like projection 123 extends forwardly from the handle 121. The finger-like projection 123 is wider at its outermost end, where a groove 124 is located. The groove 124 is shaped to matingly engage and hold a portion of the retaining ring 30.

A clamp 125 is slidably mounted to the condical tip 122 of handle 121 opposite the projection 123. The clamp 125 defines a groove 126 which is shaped to matingly engage and hold a portion of the retaining ring, 30 as best seen in FIG. 15. The clamp 125 is biased by a spring 127 toward the projection 123, wherein the clamp 125 and the projection 123 cooperate to hold the retaining ring 30 therebetween.

A slidable button 130 is positioned on the side of the handle 212 for convenient thumb manipulation, and is connected to a thin wire 131 to the clamp 125. Thus, manipulation of the button 130 will pull back the clamp 125 against spring 127, thereby releasing the ring 30 held between the clamp and the projection 123.

It should be noted that the projection 123 and the clamp 125 embrace a sufficient amount of the circumference of the retaining ring 30 to adequately hold and support it, but also leave a significant portion of the ring free. Coupled with the conical tip 122 of the handle 121 and the triangular shape of the projection 123, good visibility of the retaining ring, artificial intraocular lens, and eye is provided for the ophtalmologic surgeon using the instrument 120.

The instrument 120 further comprises a barrel 135 which is slidably received inside the tubular handle 121. A thumbwheel 136 is attached for freewheeling rotation to the upper end of handle 121, and a threaded stud 140 extends inwardly from thumbwheel 136 and is received in an interiorly threaded opening 141 in the upper end of barrel 135. Thus, rotating the thumbwheel 136 drives the barrel 135 upwardly or downwardly within and relative to the handle 121, depending upon the direction of rotation of the thumbwheel and the driven motor so imparted is both slow and controlled.

The artificial intraocular lens 10 is attached to the instrument 120 by a bridle 145. As best seen in FIG. 14, the bridle 145 comprises a generally triangular loop terminating in a tail 146. The tail 146 passes through an opening 132 in the end of the conical tip 122 of handle 121. A threaded clip 147 is secured to the end of the tail 146, and the clip 147 is threaded into an opening in the lower end of barrel 135 (see FIG. 13). Again referring to FIG. 14, the bridle 145 comprises a generally triangular loop having legs 148 – 150. Leg 148 extends from the tall 146 to drain hole 17 located near the edge of the lens 110. The bridle passes through the drain hole 17 and leg 149 of the bridle extends across the underside of the lens 110 to drain hole 19 opposite drain hole 17. The bridle also passes through drain hole 19, and the third leg 150 of the bridle extends from drain hole 19 to the tail 146. The bridle 145 is preferably fabricated of a combination of a relatively thick semirigid wire, which may be plastic, and relatively thin and very flexible thread. The relatively thick, semirigid wire is used to form the tail 146 and leg 148 of the bridle 145, leg 148 extending from the tail 146 to the drain hole 17. The thin thread is used to form the legs 149 and 150 of the triangular loop of bridle 145 which extends across the underside of the lens 10, through the drain hole 19 and back to the tail 146. Thus, when it is desired to remove the bridle 145 from the lens 10 after the lens has been implanted in an eye, the leg 150 of the triangle may be cut and the thin thread pulled through the drain hole 19 across the back of the lens and out through drain hole 17. It would be unacceptable to pull the thick semirigid wire across the back of the lens after the lens has been implanted in an eye because of the risk of rupturing the hyloid membrane, but at least a portion of the bridle must be fabricated of such thick, semirigid wire in order that the bridle be capable of at least partially supporting the lens 10 for handling and manipulating the lens during implantation.

The bridle 145 connects the artificial intraocular lens 10 with the slidable barrel 135 of the instrument 120, and therefore rotation of the thumbwheel 136 in the desired direction causes relative movement of the lens 10 toward the retaining ring 30, being carried on the instrument 120 as described above.

Referring now to FIG. 17, the instrument 120 is shown being used in the implantation of the artificial intraocular lens 10 and its associated retaining ring 30 in eye 40. It will be appreciated that the pupil can be sufficiently dilated with the use of drugs to permit the passage of the lens 10 into the posterior chamber 63 of the eye. The stiff leg 148 of the bridle 145 provides a sufficiently strong connection between the handle of instrument 120 and the lens 10 that the instrument can be used to aid in manipulating the lens into the position shown in FIG. 17. Once the lens is so positioned and the iris 52 is placed over the posts of the lens, the thumbwheel 136 of instrument 120 is rotated to draw the bridle 145 into the instrument 120 through the opening 132 in tip 122. In order to avoid pulling the lens 10 against the iris, the surgeon moves the instrument 120 and the retaining ring 30 carries thereon toward the lens as the thumbwheel 136 is rotated.

Because the opening 132 in the tip 122 of the instrument 120 is centrally located above the retaining ring 30 held between the projection 123 and the clamp 125 (see FIG. 15) and because of the symmetrical arrangement of the posts are drain holes of the lens 10, the instrument 120 presents the lens 10 to the retaining ring 30 such that the posts 12 – 15 of the lens 10 are positioned for entry into the slot 31 on the underside of the retaining ring 30. The instrument 120 provides sufficient clearance for the surgeon using it to see if the posts are properly positioned with respect to the retaining ring. After having done so, the retaining ring is press fit on to the posts by further drawing up the bridle 145 through rotation of thumbwheel 136. As shown in FIG. 17, the iris may be pushed down over the posts simultaneously with press fitting the retaining ring onto the posts; however, the posts may be pushed through the iris prior thereto.

After the retaining ring has been seated on the posts of the lens, the thin leg 149 of bridle 145 may be cut, the retaining ring release from the instrument 120 through drawing back clamp 125, and the instrument 120 and bridle 145 removed from the eye. Thereafter, the surgeon may close the eye in accordance with normal surgical techniques.

The instrument 120 offers several important advantages in implanting artificial intraocular lenses and press fitting retaining members thereon, as described above. First, it accomplishes the centering of the retaining ring or other retaining member on the posts of the lens and press fits the retaining ring onto the posts without need for manual manipulation. Thus, such positioning and press fitting are well within the range of the average ophthalmologic surgeon. Second, the press fit of the retaining ring on to the posts of the lens is achieved gently and with no pulling, ppushing, or jerking on the delicate anatomical structures of the eye. Further, the instrument affords positive control over the lens and the retaining ring during implantation thereof. Another advantage is that the implantation instrument is relatively quick, and most surgeons strongly prefer to have the eye opening for as short a time as is possible.

The instrument 120 has the still further advantage of being capable of modification for use in removing an artificial intraocular lens from an eye, if such removal is necessitated for any reason. Referring now to FIG. 18, the instrument 120 is shown with the projection 123 and the clamp 125 engaged on the retaining ring 30 which is attached to the posts of the artificial intraocular lens 10. A foot 152 is rigidly connected by a shaft 153 to the barrel 135 of the instrument 120. Therefore, rotation of the thumbwheel 136 in a direction which drives the barrel 135 downwardly within the handle 132 also drives the foot 152 against the top surface of the lens 10, and thereby accomplishes prying the retaining ring 30 from its retained position on the posts. The removal of the retaining ring is easily controlled to avoid jerking, pulling, or pushing the lens or the associated retaining ring within the eye.

Also shown in FIG. 18 is a snare 155 comprising expansible jaws 156 controlled via a control button 157, the jaws being shown clamped through drain hole 17 of the lens 10. The snare 155 is useful to retain control over the lens after the retaining ring has been removed and after the iris has been removed from the posts.

Figure 20:
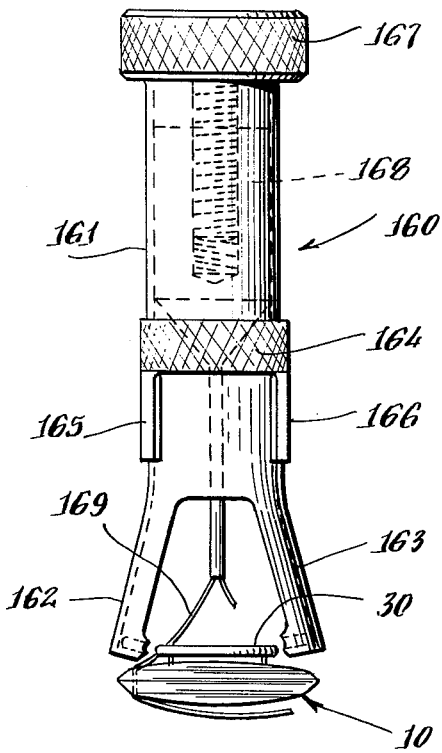
FIG. 20 is a side elevation view of the instrument of FIG. 19 expanded to release the retaining ring.

Referring now to FIGS. 19 and 20, there is shown another instrument 160 for use in implanting artificial intraocular lens as described above, and particularly in press fitting retaining members thereon. The instrument 160 generally comprises a tubular handle portion 161 terminating in two downwardly depending legs 162 and 163, which are designed to partially embrace and hold a retaining ring 30 therebetween.

In their free position, shown in FIG. 20, the legs 162 and 163 spread apart to insert or release the retaining ring 30.

A band 164 is slidably positioned around the handle 161 of the instrument 160, and the band 164 includes two tabs 165 and 166. When the band is urged downwardly along the handle 161, the tabs 165 and 166 engage the legs 162 and 163 and force them inwardly, so that they engage and hold the retaining ring 30.

The instrument 160 is provided with a thumbwheel 167 and a barrel 168 slidably mounted and driven within the handle 161 by the thumbwheel 167 in a similar manner to that described above with respect to the instrument 120. The barrel 168 is connected to the artificial intraocular lens 10 by a bridle 169, wherein rotation of the thumbwheel 167 causes relative movement of the retaining ring 30 towards the lens 10 and ultimately results in press fitting the retaining ring 30 onto the posts of the lens 10. After the retaining ring 30 has been secured to the lens 10, the band 164 is moved upwardly along the handle 161, permitting the legs 162 and 163 to spring free and release the retaining ring 30.

Good visibility for the surgeon using the instrument 160 is provided between the legs 162 and 163. Instrument 160 can also be provided with a foot and be used to remove the retaining ring from the lens, if desired.

Figure 21:
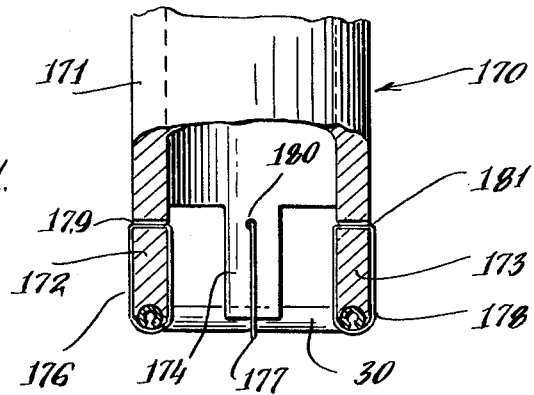
FIG. 21 is a side elevation view of an artificial intraocular lens, a retaining ring therefor, and another instrument for implanting the same within an eye, all according to the invention herein.
Figure 22:
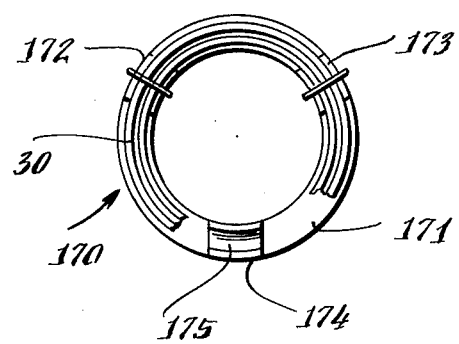
FIG. 22 is a bottom plan view of the instrument of FIG. 21.

FIGS. 21 and 22 illustrate another instrument 170 for inserting an aritificial intraocular lens into an eye and for attaching a retaining member thereto, according to the invention herein. The instrument 170 comprises a handle 171 which houses a slidably mounted barrel controlled by a thumbwheel, now shown but similar to that described above. Protruding downwardly from the handle 171 are legs 172 – 174. As best seen in FIG. 22, the bottom surfaces of the legs 172 – 174 define concave grooves, such as groove 175 of leg 174, and the concave grooves together matingly receive portions of a retaining ring 30. The retaining ring 30 may be secured to the instrument 170 by thread loops 176 – 178 passed around the underside of the retaining ring and respectively through openings 179 – 181 in the upper portion of the legs 172 – 174. A bridle connects an artificial intraocular lens to the barrel of the instrument 170, similar to the manner described above and not shown in FIGS. 21 and 22, wherein the lens is driven relative to the retaining ring for press fitting the retaining ring over the posts of the lens. Thereafter, the thread loops 176 – 178 which connect the retaining rings 172 – 174 may be severed along with the bridle, and the instrument 170 removed. The instrument 170 comprises the fewest parts of the instruments described herein while retaining most of the advantages of the other instruments, and hence is a good choice for manufacture as a disposable article.

Figure 23:
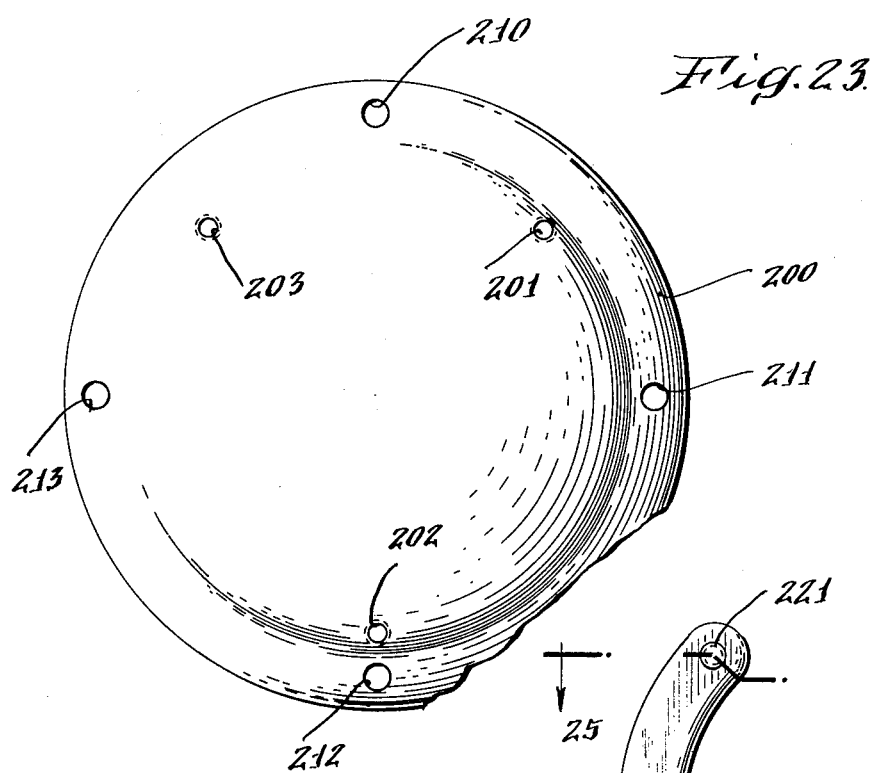
FIG. 23 is a front elevation view of another embodiment of an artificial intraocular lens according to the invention herein.
Figure 24:
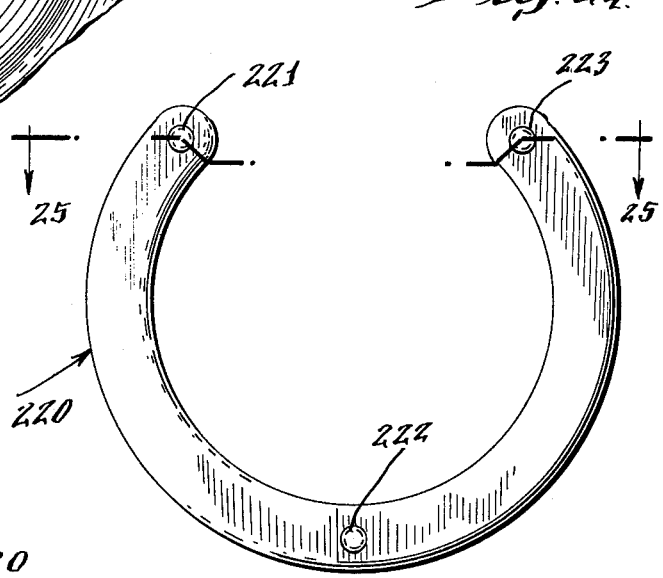
FIG. 24 is a rear elevation view of a retaining ring according to the invention herein for the artificial intraocular lens of FIG. 23.
Figure 25:
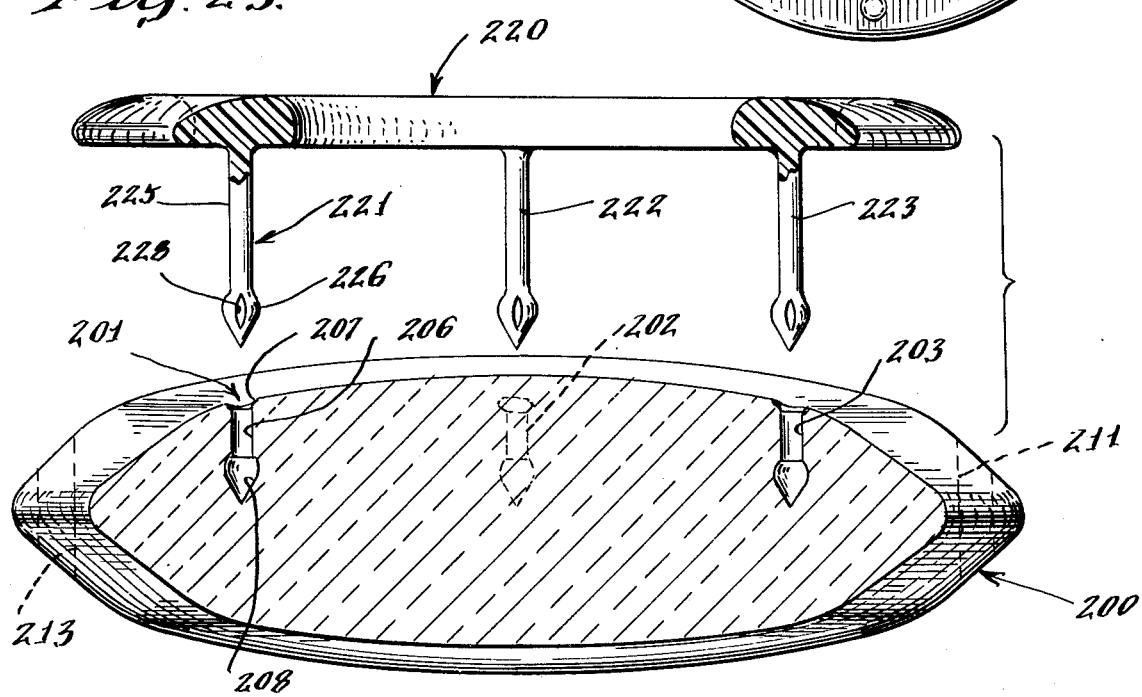
FIG. 25 is a side sectional view of the artificial intraocular lens of FIG. 23 and the retaining ring of FIG. 24.

Referring now to FIGS. 23 – 25, there is shown an artificial intraocular lens comprising an optical zone or lens portion 200 and a retaining ring 220 for anchoring the lens 200 in an eye, all according to another embodiment of the invention herein.

The lens 200 may be either a bi-convex or plano-convex lens, as required. It is preferable that it be shaped similar to the actual intraocular lens so far as is possible. The lens is preferably round in plan view and may have a diameter of 8 to 10 millimeters, as discussed with respect to lens 10 above. The lens is preferably fabricated of a medical grade of polymethyl methacrylate or of another suitable material.

The retaining ring 220 is a partial ring, as viewed in plan in FIG. 24, anticipating its use in an eye having a sector iridectomy performed thereon in a manner similar to that illustrated in FIG. 7 with respect to an earlier embodment. It will be understood that a full ring may also be used, particularly if no iridectomy is to be performed. As best seen in FIG. 25, the retaining ring 220 has a teardrop shaped cross section and is thinner near the outer edge and is rounded on its top surface. The maximum thickness of the retaining ring 220 is preferably ½ to 1 millimeter.

Protruding from the bottom of the retaining ring 220 are three posts 221 – 223, which serve to attach the retaining ring 220 to the artificial intraocular lens 200. Posts 221 and 223 are located adjacent to the ends of the partial ring, and post 222 is centrally located therebetween. Post 221 comprises a stem portion 225 and an enlarged head portion 226, which terminates in a pointed tip 227. An opening 228 is formed transversely through the enlarged heat 226 and permits the head 226 to collapse to the diameter of the stem 225 for inserting the post into openings in the lens 200, as described below. Posts 222 and 223 are similar. The retaining ring 220 and the posts 221 – 223 are preferably integral, and fabricated of polymethyl and methacrylate or other suitable material. The retaining ring may be tinted to the color of the iris of the eye which it is being implanted for cosmetic reasons, if desired.

Referring now to FIG. 23, the lens 200 is provided with three openings 201 – 203 which receive respectively the posts 221 – 223 of the retaining ring 220. The opening 201 – 203 are arrayed on a circle concentric with and near the periphery of the lens 200, and are spaced apart along the circle so that the openings 201 – 203 align with the posts 221 – 223, as best seen in FIG. 25. The lens 200 is further provided with four openings 210 – 213 adjacent the periphery thereof, and the opening 210 – 213 are positioned at 90 degree intervals about the lens. The openings 210 – 213 extend through the lens, and provide drain passageways for aqueous produced by the ciliary body when the lens 200 is implanted in an eye, and also provide for attaching a bridle to the lens to aid in implantation and/or removal thereof, as will be described more fully below.

As best seen in FIG. 25, opening 201 includes a cylindrical central portion 206 of slightly larger diameter than the stem 225 of post 221. A beveled portion 207 surrounds opening 201 at the top surface of the lens 200. Opening 201 terminates partially through the lens 200 in a generally tear shaped portion 208, which is adapted to matingly receive the enlarged head 226 of post 221. The other openings 202 and 203 are similar in shape.

Figure 26:
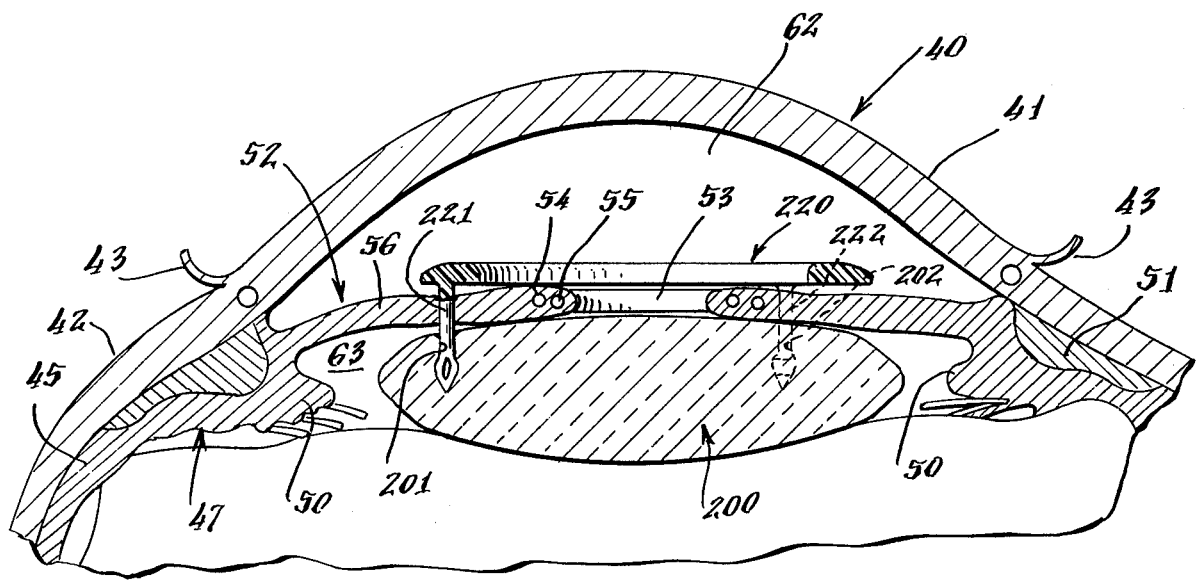
FIG. 26 is a sectional view of an eye showing the artificial intraocular lens and retaining ring of FIG. 25 implanted therein.
Figure 27:
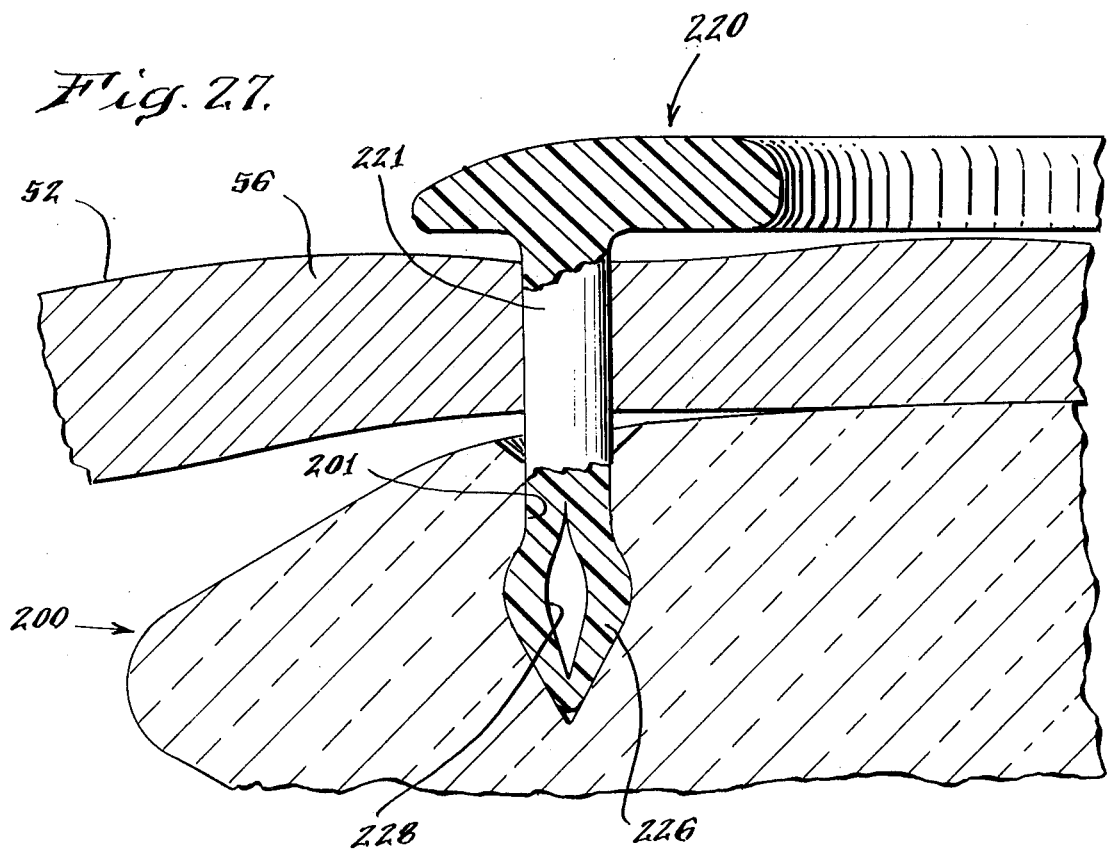
FIG. 27 is a fragmentary enlarged sectional view of a portion of the eye off FIG. 26 having the artificial intraocular lens and retaining ring implanted therein.

Referring now to FIGS. 26 and 27, there is shown an eye 40 having an artificial intraocular lens 200 and retaining ring 220 described above implanted therein. The eye 40 is the same as shown in FIG. 4 described above, and the parts of the eye have the same numbers. These parts include the cornea 41, the sclera 42, the choroid 45, the ciliary body 47, and the ciliary process 50. The eye 40 further includes the iris 52 defining a pupil 53 and having sphincter and dilator muscles 54 and 55, respectively, and stroma tissue 56. The eye 40 has an interior chamber 62 and a posterior chamber 63.

The artificial intraocular lens 200 is positioned in the posterior chamber 63 of eye 40 underlying the iris 52, and is in substantially the same position as the natural lens of the eye, removed prior to implanting the artificial intraocular lens, and, accordingly, not shown in the drawings. In order to implant the aritifical intraocular lens 200 and the associated retaining ring 220, an incision is made in the cornea 41 and the cornea is folded back. The pupil 53 can be dilated sufficiently through the use of drugs to permit passage of the artificial intraocular lens 200 through the pupil into the posterior chamber 63 of the eye. It should be noted that the artificial intraocular lens 200 is easily inserted into the posterior chamber as no posts protrude therefrom. After the lens 200 is in position in the posterior chamber, the retaining ring 220 is positioned above the iris with the pointed tips of posts 221 – 223 above openings 201 – 203. The posts 221 – 223 are inserted through the iris, and by virtue of their pointed tips, they capture no iris material. The bevels, such as bevel 207 of opening 201, guide the posts into the opening 201 – 203. The retaining ring 220 is moved toward the lens 200 to press the posts 221 – 223 into the openings 201 – 203. The enlarged head 226 of post 221 collapses, permitting the enlarged head to pass through the central portion 206 of opening 201. When the enlarged head 226 reaches the rounded inner portion 208 of opening 201, the enlarged head 226 expands and substantially fills the opening. This creates an interengaging "snap" fit between the opening 201 and the post 221. The remaining posts 222 and 223 and openings 202 and 203 cooperate similarly to hold the lens 200 and retaining ring 220 together. After implantation of the lens 200 and retaining ring 220, the ophthalmologic surgeon may then close the eye in accordance with ordinary surgical techniques.

It should also be noted that the configuration of posts 221 – 223 and openings 201 – 203 permit the posts to be withdrawn from the openings in order to release the retaining ring, if necessary.

The posts have a length approximately 2½ to 3 millimeters and support the retaining ring 220 approximately 1 to 1½ millimeters above the surface of the lens 200. It should be noted that the lens 200 and the retaining ring 220, when implanted in the eye 40, provide more clearance between the retaining ring 220 and the endothelium or interior surface of the cornea 41 than is provided with the lens 10 and the retaining ring 30 described above. The tear drop sectional shape of the retaining ring 220 aids in achieving greater clearance, as the retaining ring is thin at its outer edge. The clearance, of course, depends upon the particular eye in which the lens and retaining ring are implanted, but a clearance of approximately 1½ millimeters is normally expected with the lens 200 and retaining ring 220. The lens 10 and retaining ring 30 provide a clearance between the retaining ring and the endothelium of the cornea of slightly less than 1 millimeter, which is acceptable, but not as advantageous as the clearance provided by this emodiment.

As in previous embodiments, the retaining ring 220 is sufficiently spaced from the lens 200 so that the iris is not pinched or constricted, and the structure of the lens 200 and retaining ring 220 holds the lens firmly in the eye. The lens 200 and retaining ring 220 also do not compromise the five key ocular anatomical areas, to wit, the endothelium of the cornea; Schlemm's canal; the dilator and constrictor muscles of the pupil; the ciliary body; and the vitreous humor and hyloid membrane. Thus, complications after implantation of the artificial intraocular lens and retaining ring are greatly reduced. The position of the lens in the posterior chamber also aids in guarding against forward displacement of the vitreous humor and consequent retinal detachment. In addition, the positioning of the lens in the posterior chamber of the eye provides for restoration of good binocular vision, and the position of the retaining ring does not interfere with the field of vision.

It will be appreciated that the number of posts depending from retaining ring 220, the configuration of the posts and openings in the lens for retaining the posts, and other details, may be altered without departing from the scope of the invention herein.

Also provided according to the invention herein is an instrument 250 particularly well adapted for implanting the artificial intraocular lens 200 and associated retaining ring 220 in an eye. The instrument 250 aids in inserting the artificial intraocular lens 200 into the posterior chamber behind the iris. It also accomplishes positioning of the retaining ring 220 and the integral posts 221 – 223 with respect to the post receiving openings 201 – 203 in the artificial intraocular lens, and press-snap fitting the posts into the lens. The instrument 250 is also well adapted for implanting the other embodiments of artificial intaocular lenses and retaining means therefor described above, and in particular, for press fitting the retaining means onto the posts extending through the iris from the lens.

The instrument 250 is illustrated in FIGS. 28 – 32. It comprises a handle 260 which is stepped at 261 and thereby divided into a thin forward portion 262 well adapted for work near the eye and a thicker rear portion 263 of a size which is comfortable in gripping and manipulating the instrument. The handle 260 defines a cylindrical opening 264 along its axis, and the forward portion 262 of the handle 260 defines an outwad flared bevel or collet 265 at the forward end of opening 264. At the opposite or rear end of the handle, the opening 264 includes an enlarged portion 266 accommodating an interiorly threaded thumbwheel 268, which is mounted in a free wheeling manner to the end of handle 260 via inturned flange 267.

A shaft 270 is slidably received in the opening 164 in the handle 260. A portion of the shaft 170 extends forwardly of the handle 260 and includes two split ends 271 and 272 which are biased apart, as best seen in FIG. 32. The split ends 271 and 272 are enlarged with respect to the diameter of shaft 270 received in the opening 264, and the split ends 271 and 272 are provided with beveled surfaces 273 and 274, respectively. When the shaft 270 is retracted into the handle 260, as shown in FIGS. 28 and 29, the bevels 273 and 274 engage the collet 265 of the handle 260 and force the split ends 271 and 272 together. However, when the shaft 270 is extended forwardly with respect to the handle 260, the split ends are permitted to separate, as shown in FIG. 32.

A capture head 275 is integral with the split ends 271 and 272 of shaft 270. The capture head 275 comprises two generally semicircular discs 276 and 277 mounted to or integral with split ends 271 and 272, respectively. The discs 276 and 277 are further respectively provided with peripheral depending concave flanges 278 and 279, which are adapted to grip and hold the retaining ring 220 when the split ends 271 and 272 are biased together. When the shaft 270 is moved forward and the split ends 271 and 272 separate, the retaining ring 220 is released. Other retaining rings, described above, such as retaining ring 30 or 70, are releasably gripped by the capture head 275 in the same manner.

The instrument 250 further means for retracting the shaft 270 to capture and hold the retaining ring 220 and for extending the shaft 270 forward to release the retaining ring. These means include a drive collar 280 rotatably and slidably mounted about portion 263 of handle 260. The drive collar has a pin 281 mounted therein, and the pin 281 extends inwardly from the drive collar 280 through a diagonal slot 269 defined by the handle 260 and is received in a slot 283 defined crosswise in the shaft 270. A pin 284 mounted in the handle 260 extends into a longitudinal slot 285 formed in the shaft 270, and restrains the shaft 270 from rotational movement with respect to the handle 260. Thus, when the drive collar 280 is rotated to the position shown in FIG. 29, the pin 281 is positioned near the rear end of diagonal slot 269, and retracts the shaft 270 into the handle 260, thereby engaging the bevels 273 and 274 of the split ends with the collect 265 of the handle and urging the split ends together. When the drive wheel is rotated and moved forwardly along the handle 260, the pin 281 is positioned near the forward end of slot 269, and the pin 281 extends the shaft 270 forward to permit the split ends 271 and 272 of shaft 270 to separate.

The shaft 270 also defines an opening 286 along its axis, in which is carried a hollow rod 290. The hollow rod 290 extends forwardly of the capture head 275 and terminates in an offset foot 291. The foot 291 includes a bottom surface 298 against which the artificial intraocular lens 200 is held by a bridle 292. The bridle 292 may comprise a long strand of heavy suture material which extends inside the hollow rod 290 to the foot 291, where it departs from the hollow rod at opening 299. The bridle 292 is looped around the lens 200, passing through two of the drain openings 211 and 213, which are diametrically opposed. The foot 291 further includes two notches 293 and 294, which are diametrically opposed, and which serve to guide the bridle from the foot and also serve to hold the lens from rotating with respect to the foot. Alternatively, the foot 291 may comprise a suction fitting to hold the lens via suction applied through rod 290.

It should be noted that the foot 291 is also adapted to hold the other embodiments of lenses described above, such as lens 10.

The opposite end of the hollow rod 290 is provided with a threaded sleeve 295, which may be press fit over the rod 290, and the threaded sleeve 295 mates with the interiorly threaded thumbwheel 268. Thus, rotation of the thumbwheel 268 drives the rod 290 together with foot 291 and lens 200 attached thereto away from or toward the capture head 275. The threaded sleeve 295 extends through the thumbwheel 268, and a threaded cap 296 is attached over the end of the threaded sleeve, engaging the bridle 292. More particularly, the bridle 292 may be pulled tight and secured in its tight condition holding the lens against the foot by means of cap 296.

The rod 290 includes a slot 287 into which pin 284 extends, thereby preventing rotation of rod 290 with respect to shaft 270 and handle 260. Thus, the lens 200 and the retaining ring 220 can be accurately positioned such that the posts 221 – 223 will enter the openings 201 – 203 as thumbwheel 268 is rotated to move the retaining ring and lens together.

The instrument 250 is used in implanting the artificial intraocular lens 200 and the retaining ring 220 in the following manner. First, the retaining ring 220 is positioned in the capture head 275 and the drive collar 280 is rotated to retract shaft 270 into the handle 260, thereby urging the split ends 271 and 272 closed to firmly grip the retaining ring 220. The artificial intraocular lens 200 is held against the bottom surface 298 of foot 291 of rod 290 by passing the bridle 292 through the drain holes 211 and 213, aligning the bridle in the notches 293 and 294, and tightening the bridle and securing it in its tightened position by cap 296. Thumbwheel 268 is rotated to extend the rod 290 and the lens 200 forward with respect to the handle. With the lens so extended, the instrument 250 is used to insert the lens through the pupil to its position underlying the iris. Thereafter, thumbwheel 268 is rotated to cause relative movement of the retaining ring 220 toward the lens 200, the surgeon taking care to move the handle forwardly to bring the retaining ring 220 into position over the lens and not to pull the lens back through the pupil. Inasmuch as the retaining ring 220 is firmly held by the capture head and the lens 200 is firmly held against the foot 291, and the retaining ring and the lens are positioned such that the posts 221 – 223 of the retaining ring are presented to the openings in the lens, further rotation of thumbwheel 268 causes the posts 221 – 223 to puncture the iris and press-snap into the openings 201 – 293 in lens 200. The bevels surrounding the openings 201 – 203 aid in guiding the posts into the openings. Some flexure of the posts occurs during this procedure, but it is insufficient to cause damage to the posts.

Once the retaining ring 220 is attached to the lens 200 via the posts 221 – 223, drive collar 280 is rotated to release the retaining ring from the capture head 275. Threaded cap 296 is then rotated to release the bridle 292 so that the instrument can be withdrawn. The bridle is then severed and removed from around the lens 200.

The instrument 250 is used in the same manner in implanting other embodiments of artificial intraocular lenses, such as lens 10 and retaining ring 30, except that the instrument then operates to press the retaining ring onto the posts.

The instrument 250 may also be used to remove retaining rings from previously implanted lenses by gripping the retaining ring in the capture head and thereafter driving the foot 291 forward by means of thumbwheel 268.

It will be apparent to those skilled in the art that various modifications of the artificial intraocular lenses and instrments described herein can be made without departing from the spirit and scope of the invention. For instance, the number of posts and the precise positioning of the posts may be altered, and similarly, the number of drain holes and their positions can be altered. Other materials may be suitable for fabricating artificial intraocular lenses according to the invention herein, and the materials disclosed herein merely provide acceptable examples. The sizes of the artificial intraocular lenses may be changed, particularly when the lenses are to be used in animals. The lenses may be somewhat thinner than the natural lens, whether human or animal, and such thinner lenses are nevertheless considered as being shaped "similar" to the natural lens. The instruments may also be modified, as for instance to accept various configurations of retaining members. Similarly, the thumbwheel drive means could be replaced by other drive means achieving relative movement between an artificial intraocular lens and a retaining member therefor. Also, other means for holding and manipulating the lenses may be employed. For instance, the artificial intraocular lenses can be held and manipulated by conventional forceps, or by provision of a flexible tipped instrument having an opening therethrough to which suction is applied, wherein the lens is held to the instrument by vacuum and released from the instrumenht by releasing the suction. With respect to the technique of implanting the artificial intraocular lenses described herein, various ophthalmologic surgeons may develop different techniques dictated by their own skills and preferences.

The artificial intraocular lenses, retaining members, and instruments for implantation thereof described above are believed to efficiently achieve the objects of the invention. The usefulness and advantages of the artificial intraocular lenses, retaining members, and the instruments aiding implantation thereof will be readily apparent to those skilled in the art.

Accordingly, the above description of the preferred embodiments is to be construed as illustrative only rather than as limiting, and the scope of the invention is defined in the following claims.

We claim:

1. An artificial intraocular lens for implantation in the posterior chamber of an eye, the artificial intraocular lens comprising an optical zone portion fabricated of transparent material and shaped similar to a natural lens, a plurality of posts attached to the optical zone portion near the periphery thereof and extending forwardly therefrom, and retaining means adapted to be secured to the ends of said posts, wherein said artificial intraocular lens may be implanted in the posterior chamber of an eye with the posts protruding forwardly from the optical zone portion through the iris and into the anterior chamber of the eye, and wherein said retaining means may be secured to the ends of the posts in the anterior chamber of the eye, wherein said posts and retaining means together hold and position the lens within the eye and prevent the posts from pulling through the iris thereof.

2. An artificial intraocular lens as defined in claim 1 wherein said retaining means comprises one retaining member for each of said plurality of posts.

3. An artificial intraocular lens as defined in claim 1 wherein said retaining means comprises more than one retaining member, each of which is adapted to be secured to the ends of two or more of said plurality of posts.

4. An artificial intraocular lens as defined in claim 1 wherein said retaining means is a single retaining member adapted to be secured to each of said plurality of posts.

5. An artificial intraocular lens as defined in claim 4 wherein a single retaining member comprises a closed retaining member connecting all of said plurality of posts, said closed retaining member having an opening therethrough which is positioned above the pupil of an eye into which the artificial intraocular lens is implanted.

6. An artificial intraocular lens as defined in claim 1 wherein said plurality of posts are positioned on a circle concentric with the edge of the optical zone portion, and wherein said retaining means comprises a retaining ring adapted to be secured to each of said posts.

7. An artificial intraocular lens as defined in claim 6 wherein each of said posts has an enlarged head portion at its outer end, and wherein said retaining ring has a slot configured for an interengaging fit over the enlarged head portions of the posts, and wherein said retaining ring is sufficiently flexible to admit the enlarged head portions of said posts into said slot, the retaining ring thereby being adapted to be secured to the posts by a press fit.

8. An artificial intraocular lens as defined in claim 7 wherein said plurality of posts comprises four posts deployed at 90° intervals about said circle.

9. An artificial intraocular lens as defined in claim 1 wherein said posts and said retaining means are configured for an interengaging fit, wherein said retaining means are adapted to be secured to said posts by a press fit.

10. An artificial intraocular lens as defined in claim 9 wherein each of said posts has an enlarged head portion and wherein said retaining means define openings configured for an interengaging fit with the enlarged head portions of said posts, wherein said retaining means are adapted to be secured to said posts by a press fit.

11. An artificial intraocular lens as defined in claim 10 wherein the openings in said retaining means extend partially therethrough.

12. An artificial intraocular lens as defined in claim 1 wherein said posts and said retaining means are fabricated of materials which are sonically weldable together, wherein said retaining means are adapted to be secured to said posts by sonic welding.

13. An artificial intraocular lens as defined in claim 1 wherein said retaining means and said posts are fabricated of materials laser weldable together, wherein said retaining means are adapted to be secured to said posts by laser welding.

14. An artificial intraocular lens as defined in claim 1 wherein each of said posts is threaded along an end portion thereof, and wherein said threaded end portions of said posts are received in matingly interiorly threaded openings in said optical zone portion to mount said posts to said optical zone portion.

15. An artificial intraocular lens as defined in claim 1 wherein said posts are press fit into mating openings in said optical zone portion to mount said posts thereto.

16. An artificial intraocular lens as defined in claim 15 wherein said posts and said optical zone portion are sonically welded together.

17. An artificial intraocular lens as defined in claim 1 wherein said optical zone portion defines at least one opening therethrough and near the periphery thereof, said opening being adapted to receive a means aiding in the insertion or removal of said artificial intraocular lens and to permit the free flow of aqueous through the optical zone portion thereof.

18. An artificial intraocular lens as defined in claim 17 wherein said at least one opening comprises two openings diametrically opposed across said optical zone portion.

19. An artificial intraocular lens as defined in claim 8 and further comprising four openings defined by said optical zone portion near the periphery thereof, and four openings arrayed at 90° intervals about said optical zone portion and each of said openings positioned 45° from the adjacent posts.

20. An artificial intraocular lens as defined in claim 1 wherein said optical zone portion is fabricated of polymethyl methacrylate.

21. An artificial intraocular lens as defined in claim 1 wherein said optical zone portion is fabricated of silicone.

22. An artificial intraocular lens as defined in claim 17 and further comprising an insertion bridle including a semi-rigid elongated member removably attached to said optical zone portion by insertion through the opening defined thereby.

23. An artificial intraocular lens as defined in claim 18 and further comprising an insertion bridle therefore, the insertion bridle including: a substantially triangular loop the first leg of which begins at one of said openings and extends away from the optical zone portion, said first leg being fabricated of a semi-rigid material; a second leg extending across the underside of the optical zone portion between said two openings, said second leg being fabricated of a thin, flexible material; a third leg extending from the other of said openings and converging with said first leg, said third leg being fabricated of a thin flexible material; and a tail portion joining said first and third legs at the point at which they converge and extending away therefrom.

24. An artificial intraocular lens as defined in claim 9 and an instrument for press fitting the retaining means thereof onto the posts thereof, the instrument comprising;
 a. a handle;
 b. means releasably supporting said retaining means on said handle;
 c. means mounted on said handle and manually operable for movement away from releasably supported retaining means;
 d. a bridle extending past said releasably supported retaining means and connecting the optical zone portion of said artificial intraocular lens to said manually operable means
wherein operation of the manually operable means causes relative movement of the retaining means towards the posts extending forwardly from said optical zone portion and press fits said retaining means into engagement on said posts.

25. An artificial intraocular lens and instrument for press fitting the retaining means thereof onto the posts thereof as defined in claim 24, wherein said means mounted on said handle and manually operable for movement away from releasably supported retaining means comprises a barrel slidably mounted to said handle and manually operable means for driving said barrel away from said retaining means support means.

26. An artificial intraocular lens and instrument for attaching or press fitting the retaining means thereof onto the posts thereof as defined in claim 25 wherein said manually operable means for driving said barrel comprises a thumbwheel mounted for free-wheeling rotation on said handle, a threaded stud extending from said thumbwheel and received in a matingly threaded opening in said barrel, wherein rotation of said thumbwheel drives said barrel in relative movement with respect to said handle and to the retaining means releasably supported thereon.

27. An artificial intraocular lens and an instrument for press fitting the retaining means thereof onto the posts thereof as defined in claim 24 wherein said retaining means comprises a retaining ring and wherein said means for releasably supporting said retaining ring on said handle comprises a portion of said handle defining a groove for receiving a portion of said retaining ring, and a clamp defining another groove for receiving another portion of said retaining ring opposite said first portion, said clamp slidably mounted on said handle for releasing said retaining ring.

28. An artificial intraocular lens and an instrument for press fitting the retaining means thereof to the posts thereof as defined in claim 24 wherein said retaining means comprises a retaining ring and wherein said means for releasably supporting the retaining ring on said handle comprises at least two legs depending from said handle, said two legs urged together by an annular band surrounding said legs to grip and hold the retaining ring therebetween, and wherein removing said annular band from its position surrounding said legs releases said legs and the retaining ring held therebetween.

29. An artificial intraocular lens and an instrument for press fitting the retaining means thereof to the posts thereof as defined in claim 24 wherein said means for releasably supporting the retaining means on said handle comprises a plurality of legs depending from said handle and being adapted to receive said retaining means on the lower surfaces thereof, and an equal plurality of severable loops passed through openings defined in said legs and around said retaining means to secure said retaining means to said legs, said retaining means being releasable by severing said loops.

30. An artificial intraocular lens and an instrument for press fitting the retaining means thereof to the posts thereof as defined in claim 24 and wherein said retaining means comprises a retaining ring, and wherein said handle defines an opening centrally positioned above said retaining ring, said bridle symmetrically supports the optical zone portion including the posts protruding therefrom with respect to said bridle, and said bridle passes through said opening defined by said handle, the opening and bridle thereby aligning the posts of the optical zone portion with the retaining means supported on said handle.

31. An artificial intraocular lens as defined in claim 9 and an instrument for removing the retaining means thereof from its interengaging press fit onto the posts therof, the instrument comprising;
 a. a handle;
 b. means releasably supporting said retaining means on said handle;
 c. means mounted on said handle and manually operable for movement toward releasably supported retaining means;
 d. a stem extending past said releasably supported retaining means and terminating in a foot engageable against the optical zone portion of said artificial intraocular lens,
wherein operation of the manually operable means causes relative movement of the retaining means away from the posts to disengage the interengaging fit between said retaining means and said posts.

32. An artificial intraocular lens for implantation in the posterior chamber of the eye, the artificial intraocular lens comprising:
 a. an optical zone portion fabricated of transparent material and shaped similar to a natural lens;
 b. a plurality of posts attached to the optical zone portion near the periphery thereof and arrayed on a circle concentric with the periphery thereof, said posts extending forwardly from said optical zone portion;
 c. a retaining ring including an annular slot defined on the underside thereof and configured for an interengaging press fit with the ends of said posts for securing said ring to said posts; and
 d. a plurality of openings defined through said optical zone portion near the periphery thereof, at least two of said plurality of openings being diametrically opposed,
wherein said artificial intraocular lens may be implanted in the posterior chamber of an eye with the posts protruding forwardly from the optical zone portion through the iris and into the anterior chamber of the eye, and wherein said retaining ring is secured to the ends of the posts in the anterior chamber of the eye, said posts and retaining rings together holding and positioning the artificial intraocular lens within the eye and preventing the posts from pulling through the iris thereof.

33. An artificial intraocular lens as defined in claim 32 and an instrument for press fitting the retaining ring thereof to the posts thereof, said instrument comprising:
 e. a handle terminating in a conical tip at one end thereof and defining an opening at the apex of said conical tip;
 f. a projection extending from said handle adjacent to said conical tip thereof and defining a groove for receiving and holding a portion of said retaining ring;
 g. a clamp slidably mounted on said handle and defining a groove for receiving and holding another portion of said retaining ring opposite the portion of the retaining ring held by said projection, said clamp and said projection together releasably supporting said retaining ring centrally below the opening defined by the conical tip of the handle;
 h. a barrel slidably mounted in said handle and including an interiorly threaded opening formed in one end thereof;
 i. a thumbwheel mounted for free-wheeling rotation on the end of the handle opposite the conical tip thereof;
 j. a threaded stud extending downwardly from said thumbwheel and received in the interiorly threaded opening formed in the barrel, wherein rotation of the thumbwheel drives the barrel within the handle; and
 k. a bridle comprising a triangular loop passing through the diametrically opposed openings in said optical zone portion, the base of said loop extending across the underside of said optical zone portion between said openings and the remaining legs extending from said openings through the retaining ring and converging at and passing through the opening defined by the conical tip in the handle and secured to said barrel, wherein the central positioning of the opening defined by the tip of the handle with respect to the retaining ring supported on the handle causes the posts protruding forwardly from the optical zone portion to be aligned with the slot in the retaining ring, and wherein rotation of the thumbwheel causes relative movement of the ring toward the post and accomplishes press fitting of the retaining ring into interengagement with the posts.

34. An artificial intraocular lens for implantation into the posterior chamber of an eye, the artificial intraocular lens comprising an optical zone portion fabricated of transparent material and shaped similar to a natural lens, and retaining means having a plurality of posts attached thereto and extending rearwardly therefrom, the ends of said posts adapted to be secured to said optical zone portion, wherein said optical zone portion may be implanted in the posterior chamber of an eye and said retaining means may be positioned in the anterior chamber of the eye with the posts protruding rearwardly from said retaining means through the iris and into the posterior chamber of the eye where said posts are secured to said optical zone portion, said retaining means and posts thereby together holding and positioning the artificial intraocular lens within the eye.

35. An artificial intraocular lens as defined in claim 34 wherein said retaining means comprises a single retaining member having a plurality of spaced-apart posts protruding rearwardly therefrom.

36. An artificial intraocular lens as defined in claim 35 wherein a single retaining member comprises a closed retaining ring defining an opening therethrough which is positioned above the pupil of an eye into which the artificial intraocular lens is implanted.

37. An artificial intraocular lens as defined in claim 35 wherein said single retaining member comprises a partial ring.

38. An artificial intraocular lens as defined in claim 37 wherein said partial ring is substantially three-fourths of a full ring.

39. An artificial intraocular lens as defined in claim 38 wherein said partial ring and said posts are integral.

40. An artificial intraocular lens as defined in claim 38 wherein said plurality of spaced-apart posts comprises three posts.

41. An artificial intraocular lens as defined in claim 40 wherein a first one of said three posts is attached to said partial ring adjacent to one end thereof, a second one of said three posts is attached to said partial ring adjacent to the other end thereof, and a third one of said three posts is attached to said partial ring intermediate said first and second posts.

42. An artificial intraocular lens as defined in claim 41 wherein said retaining ring has a tear drop cross-sectional shape.

43. An artificial intraocular lens as defined in claim 34 wherein said plurality of posts are attached to the optical zone portion at points on a circle concentric with the edge thereof.

44. An artificial intraocular lens as defined in claim 34 wherein said posts and said optical zone portion are configured for an interengaging fit, wherein said posts are adapted to be secured to said optical zone portion by a press fit.

45. An artificial intraocular lens as defined in claim 44 wherein each of said posts has an enlarged head portion and wherein said optical zone portion defines openings configured for an interengaging fit with the enlarged head portions of said posts, wherein said posts are adapted to be secured to said optical zone portion by a press fit.

46. An artificial intraocular lens as defined in claim 45 wherein the openings in said optical zone portion extend partially therethrough.

47. An artificial intraocular lens as defined in claim 46 wherein said openings comprise an entrance passage and terminate in a rounded portion larger than said entrance passage, said rounded portion matingly receiving the enlarged heads of said posts.

48. An artificial intraocular lens as defined in claim 47 wherein the enlarged heads of said posts have openings formed therein permitting the enlarged heads to collapse and pass through said entrance passageway of said openings.

49. An artificial intraocular lens as defined in claim 34 wherein said optical zone portion defines at least one opening therethrough and near the periphery thereof, said opening being adapted to receive a means aiding in the insertion or removal of said artificial intraocular lens and to permit the free flow of aqueous through the optical zone portion therof.

50. An artificial intraocular lens as defined in claim 49 wherein said at least one opening comprises two openings diametrically opposed across said optical zone portion.

51. An artificial intraocular lens as defined in claim 34 wherein said optical zone portion is fabricated of polymethyl methacrylate.

52. An artificial intraocular lens as defined in claim 44 and an instrument for press fitting the posts of said retaining means onto the optical zone portion, the instrument comprising;
 a. a handle;
 b. means releasably holding said retaining means on said handle;
 c. means slidably mounted on said handle and extending past and terminating beyond said releasably supported retaining means, said means releasably holding said optical zone portion; and
 d. manually operable means for moving said slidably mounted means to draw said optical zone portion toward said releasably supported retaining means; wherein operation of the manually operable means causes relative movement of the optical zone portion towards the posts extending rearwardly from said retaining means and press fits said posts into engagement with said optical zone portion.

53. An artificial intraocular lens and instrument for press fitting the posts of said retaining means onto the optical zone portion as defined in claim 52 wherein said means releasably holding said retaining means on said handle comprises a shaft extending from said handle, said shaft having split ends, said split ends provided with means for gripping and holding said retaining means when said split ends are urged together and releasing said retaining means when said split ends are spaced apart.

54. An artificial intraocular lens and instrument for press fitting the posts of said retaining means onto the optical zone portion as defined in claim 53 wherein said means for gripping and holding said retaining means is a capture head comprising a split disc one portion of which is mounted to one of said split ends and the other portion of which is mounted to the other of said split ends, said split disc including flanges for receiving said retaining means.

55. An artificial intraocular lens and instrument for press fitting the posts of said retaining means onto the optical zone portion as defined in claim 53 wherein said shaft is slidably mounted in said handle, and said shaft and said handle are respectively provided with cooperating bevel and collet surfaces for urging said split ends together when said shaft is partially retracted into said handle, and further comprising means for retracting said shaft to engage said bevel and collet means and for extending said shaft to release said bevel and collet means.

56. An artificial intraocular lens and instrument for press fitting the posts of said retaining means onto the optical zone portion as defined in claim 52 wherein said means slidably mounted on said handle and releasably holding said optical zone portion comprises a rod slidably mounted to said handle, said rod terminating in a foot including a surface configured to receive the surface of said optical zone portion, and means for releasably holding said optical zone portion against the surface of said foot.

57. An artificial intraocular lens and instrument for press fitting the posts of said retaining means onto the optical zone portion as defined in claim 53 wherein said optical zone portion defines two openings near the periphery thereof, said two openings located substantially diametrically opposed in said optical zone portion, and wherein said means slidably mounted on said handle and releasably holding said optical zone portion comprises a rod slidably mounted to said handle, said rod terminating in a foot including a surface configured to receive the surface of said optical zone portion, and a bridle extending from said foot through one of said openings defined by said optical zone portion, across said optical zone portion, through the other of said openings defined by said optical zone portion and back to said foot, said bridle holding said optical zone portion against the surface of said foot.

58. An artificial intraocular lens and instrument for press fitting the posts of said retaining means onto the optical zone portion as defined in claim 57 wherein said rod is slidably mounted in said shaft and is flanked by said split ends of said shaft.

59. An artificial intraocular lens and instrument for press fitting the posts of said retaining means onto the optical zone portion as defined in claim 58 wherein said handle further comprises an interiorly threaded thumbwheel free wheelingly mounted thereon, and said rod is threadably connected to said thumbwheel, wherein rotation of said thumbwheel drives said rod relative to said handle.

60. An artificial intraocular lens and instrument for press fitting the posts of said retaining means onto the optical zone portion as defined in claim 58 wherein said handle includes means holding said shaft and said rod against rotation with respect to said handle.

61. An artificial intraocular lens for implantation into the posterior chamber of an eye, the artificial intraocular lens comprising:
 a. a retaining ring comprising substantially three-fourths of a full ring, said retaining ring having a substantially tear drop cross-sectional shape;
 b. three posts attached to and extending rearwardly from said retaining ring, the first of said posts attached to said retaining ring adjacent one end thereof, the second of said posts attached to said retaining ring adjacent the other end thereof, and the third of said posts attached to said retaining ring intermediate said first and second posts, each post comprising an enlarged collapsible head portion; and
 c. an optical zone portion fabricated of a transparent material and shaped similar to a natural lens, said optical zone portion defining three openings partially therethrough, said three openings positioned and configured to receive the three posts for attaching said retaining ring to said optical zone portion, and said optical zone portion also defining at least two openings therethrough and near the periphery thereof, said two openings diametrically opposed across said optical zone portion,
whereby said optical zone portion is adapted for positioning in the posterior chamber of an eye, and said retaining ring is adapted for positioning in the anterior chamber of the eye with said posts extending rearwardly therefrom through the iris of the eye, and said three posts are secured to said optical zone portion, by an interengaging fit between said posts and the three openings defined partially through said optical zone portion, said retaining ring and said posts holding and positioning said optical zone portion in the posterior chamber of the eye.

* * * * *

UNITED STATES PATENT OFFICE
CERTIFICATE OF CORRECTION

PATENT NO. : 3,991,426
DATED : November 16, 1976
INVENTOR(S) : Leonard Flom and Kenneth J. Rodgerson It is certified that error appears in the above-identified patent and that said Letters Patent are hereby corrected as shown below:

Column 2, line 16, "membrance" should be --membrane--.

Column 3, line 45, "intracular" should be --intraocular--.

Column 3, line 61, after "hyloid" insert --membrane, does not interfere with the constrictor and dilator--.

Column 5, line 9, "embodiment" should be --embodiments--.

Column 6, line 23, "off FIG. 26" should be --of FIG. 26--.

Column 6, line 38, "showning" should be --showing--.

Column 6, line 39, "release" should be --released--.

Column 7, line 6, "rocognized" should be --recognized--.

Column 7, line 46, "produce" should be --produced--.

Column 7, line 54, "define" should be --defined--.

Column 8, line 33, "interiro" should be --interior--.

UNITED STATES PATENT OFFICE
CERTIFICATE OF CORRECTION

Patent No. 3,991,426               Dated  November 16, 1976

Inventor(s) Leonard Flom and Kenneth J. Rodgerson

It is certified that error appears in the above-identified patent and that said Letters Patent are hereby corrected as shown below:

Column 9, line 34, "orr" should be --or--.

Column 9, line 48, "note" should be --noted--.

Column 9, line 53, "musclles" should be --muscles--.

Column 9, line 55, "there" should be --these--.

Column 10, line 8, "three-fourth" should be --three-fourths-- or --3/4--.

Column 10, line 40, "lossely" should be --loosely--.

Column 11, line 3, "cycle" should be --circle--.

Column 11, line 5, "treaded" should be --threaded--.

Column 11, line 9, delete the first occurrence of "to a head portion 101".

Column 12, line 8, insert --to-- after the word "on".

Column 12, line 18, "whih" should be --which--.

UNITED STATES PATENT OFFICE
CERTIFICATE OF CORRECTION

Patent No. 3,991,426  Dated November 16, 1976

Inventor(s) Leonard Flom and Kenneth J. Rodgerson

It is certified that error appears in the above-identified patent and that said Letters Patent are hereby corrected as shown below:

Column 12, line 25, "condical" should be --conical--.

Column 12, line 34, "212" should be --121--.
See specification page 25, line 9, as filed.

Column 12, line 35, "to" first occurrence should be -- by --.

Column 12, line 58, "motor" should be --motion--.

Column 13, line 2, "tall" should be --tail--.

Column 13, line 58, "are" should be --and--.

Column 14, line 6, "release" should be --released--.

Column 14, line 22, "ppushing" should be --pushing--.

Column 14, line 27, "opening" should be --opened--.

Column 15, line 21, "aritificial" should be --artificial--.

Column 15, line 25, "now" should be --not--.

UNITED STATES PATENT OFFICE
CERTIFICATE OF CORRECTION

Patent No. 3,991,426      Dated November 16, 1976

Inventor(s) Leonard Flom and Kenneth J. Rodgerson

It is certified that error appears in the above-identified patent and that said Letters Patent are hereby corrected as shown below:

Column 16, line 12, "heat" should be --head--.

Column 16, line 19, insert --into-- after the word "eye".

Column 16, line 24, "opening" should be --openings--.

Column 16, line 30, "opening" should be --openings--.

Column 17, line 9, "opening" should be --openings--.

Column 18, line 33, "164" should be --264--.

Column 18, line 34, "170" should be --270--.

Column 18, line 61, insert --includes-- after the word "further".

Column 19, line 10, "collect" should be --collet--.

Column 20, line 18, "293" should be --203--.

Column 20, line 68, "instrumenht" should be --instrument--.

UNITED STATES PATENT OFFICE
CERTIFICATE OF CORRECTION

Patent No. 3,991,426     Dated  November 16, 1976

Inventor(s) Leonard Flom and Kenneth J. Rodgerson

It is certified that error appears in the above-identified patent and that said Letters Patent are hereby corrected as shown below:

Column 22, line 54 (claim 19, line 3), "and" should be --said--.

Column 26, line 9 (claim 36, line 2), "a" should be --said--.

Signed and Sealed this

Twelfth Day of April 1977

[SEAL]

Attest:

RUTH C. MASON
Attesting Officer

C. MARSHALL DANN
Commissioner of Patents and Trademarks